US008221390B2

(12) United States Patent
Pal et al.

(10) Patent No.: US 8,221,390 B2
(45) Date of Patent: Jul. 17, 2012

(54) MEDICAL DEVICE DELIVERY SYSTEM HAVING A SHEATH WITH A FLARED STRAIN RELIEF MEMBER OPERATIVELY COUPLED BY A UNIDIRECTIONAL HANDLE

(75) Inventors: Dharmendra Pal, Wilmington, MA (US); Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 418 days.

(21) Appl. No.: 11/787,376

(22) Filed: Apr. 16, 2007

(65) Prior Publication Data

US 2007/0250150 A1 Oct. 25, 2007

Related U.S. Application Data

(60) Provisional application No. 60/793,709, filed on Apr. 20, 2006.

(51) Int. Cl.
*A61M 25/16* (2006.01)
*A61M 25/18* (2006.01)

(52) U.S. Cl. ....... 604/538; 604/535; 604/536; 623/1.11; 623/1.12; 606/108

(58) Field of Classification Search ................. 604/533, 604/535, 538, 523, 524, 536; 606/108; 623/1.11, 623/1.12
See application file for complete search history.

(56) References Cited

U.S. PATENT DOCUMENTS

| | | | |
|---|---|---|---|
| 4,508,367 A * | 4/1985 | Oreopoulos et al. ............. 285/3 |
| 4,580,568 A | 4/1986 | Gianturco | |
| 4,648,865 A * | 3/1987 | Aigner ........................ 604/6.09 |
| 4,781,703 A * | 11/1988 | Walker et al. ................. 604/264 |
| 5,017,259 A * | 5/1991 | Kohsai ........................... 156/294 |
| 5,035,706 A | 7/1991 | Giantureo et al. | |
| 5,282,824 A | 2/1994 | Gianturco | |
| 5,380,304 A | 1/1995 | Parker | |
| 5,507,771 A | 4/1996 | Gianturco | |
| 5,634,928 A * | 6/1997 | Fischell et al. ............... 623/1.11 |
| 5,690,644 A | 11/1997 | Yurek et al. | |
| 5,700,253 A * | 12/1997 | Parker .......................... 604/526 |
| 5,720,776 A | 2/1998 | Chuter et al. | |
| 6,174,327 B1 * | 1/2001 | Mertens et al. .............. 623/1.11 |

(Continued)

OTHER PUBLICATIONS

Brochure: "Zilver 518 Biliary-Stent," Cook Incorporated, 2005, 6 pages.

(Continued)

*Primary Examiner* — Bhisma Mehta
*Assistant Examiner* — Larry R Wilson
(74) *Attorney, Agent, or Firm* — Brinks Hofer Gilson & Lione

(57) ABSTRACT

A flared strain relief member for medical device delivery systems for stents, prosthetic valve devices, and other implantable articles inside a patient's body are provided. An elongate outer sheath has proximal and distal end portions defining a passageway, and the proximal end portion having an outer layer including melt bonding material. A strain relief member has a tubular first end portion of a first outer diameter and a flared second end portion of a greater second outer diameter. The strain relief member has an inner engaging surface that includes melt bonding material, at least a portion of which disposes concentrically about, and melt bonded to, the outer sheath proximal end portion melt bonding outer layer. The strain relief member second end portion is operatively coupled between a handle first connector and handle second connector. Methods of making a flared strain relief member for medical device delivery systems are also provided.

21 Claims, 16 Drawing Sheets

U.S. PATENT DOCUMENTS

| | | |
|---|---|---|
| 6,299,635 B1 | 10/2001 | Frantzen |
| 6,319,279 B1 * | 11/2001 | Shannon et al. .............. 623/1.44 |
| 6,380,457 B1 | 4/2002 | Yurek et al. |
| 6,589,227 B2 | 7/2003 | Klint |
| 6,592,549 B2 | 7/2003 | Gerdts et al. |
| 6,613,075 B1 | 9/2003 | Healy et al. |
| 6,723,071 B2 | 4/2004 | Gerdts et al. |
| 6,743,252 B1 | 6/2004 | Bates et al. |
| 6,755,855 B2 | 6/2004 | Yurek et al. |
| 6,939,370 B2 | 9/2005 | Hartley et al. |
| 7,115,109 B2 | 10/2006 | Gerdts et al. |
| 7,117,703 B2 | 10/2006 | Kato et al. |
| 2006/0020321 A1 | 1/2006 | Parker |
| 2006/0155357 A1 | 7/2006 | Melsheimer |
| 2006/0190069 A1 | 8/2006 | Baker-Janis et al. |
| 2006/0247661 A1 * | 11/2006 | Richards et al. .............. 606/108 |

OTHER PUBLICATIONS

Brochure: "Zilver® Vascular Stent—Instructions for Use," Cook Incorporated, Jun. 2006, 13 pages.

Digital photograph of three current product samples from Cook Incorporated believed to be representative of products sold commercially by Cook Incorporated prior to Apr. 20, 2005.

* cited by examiner

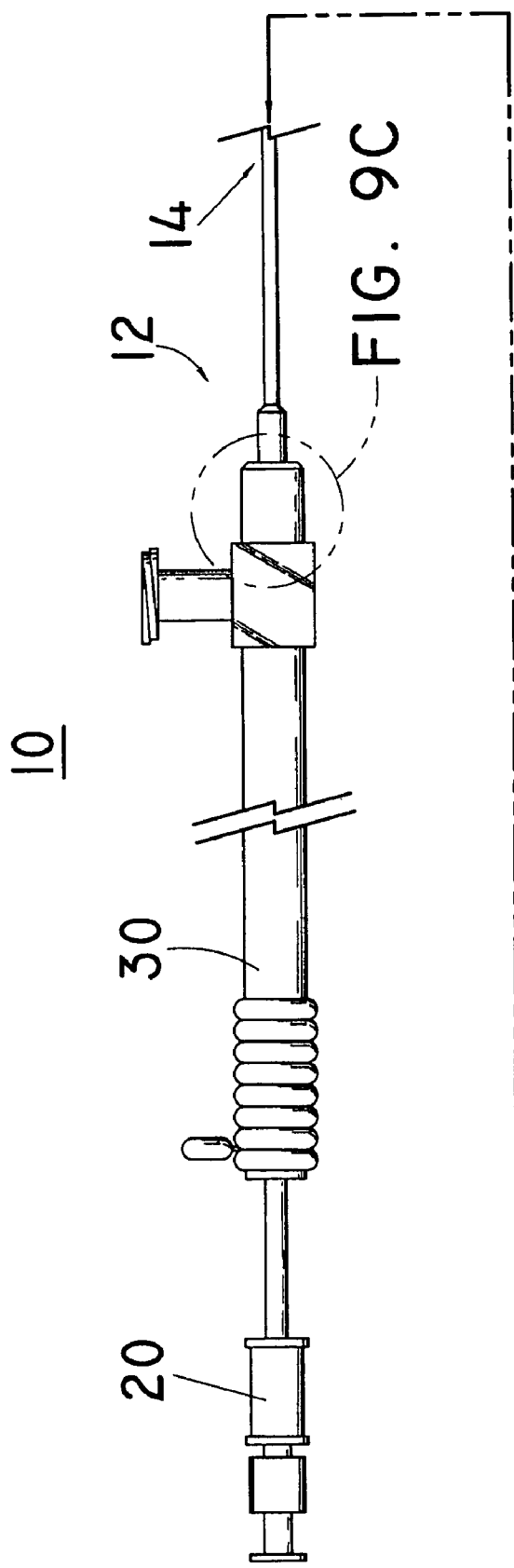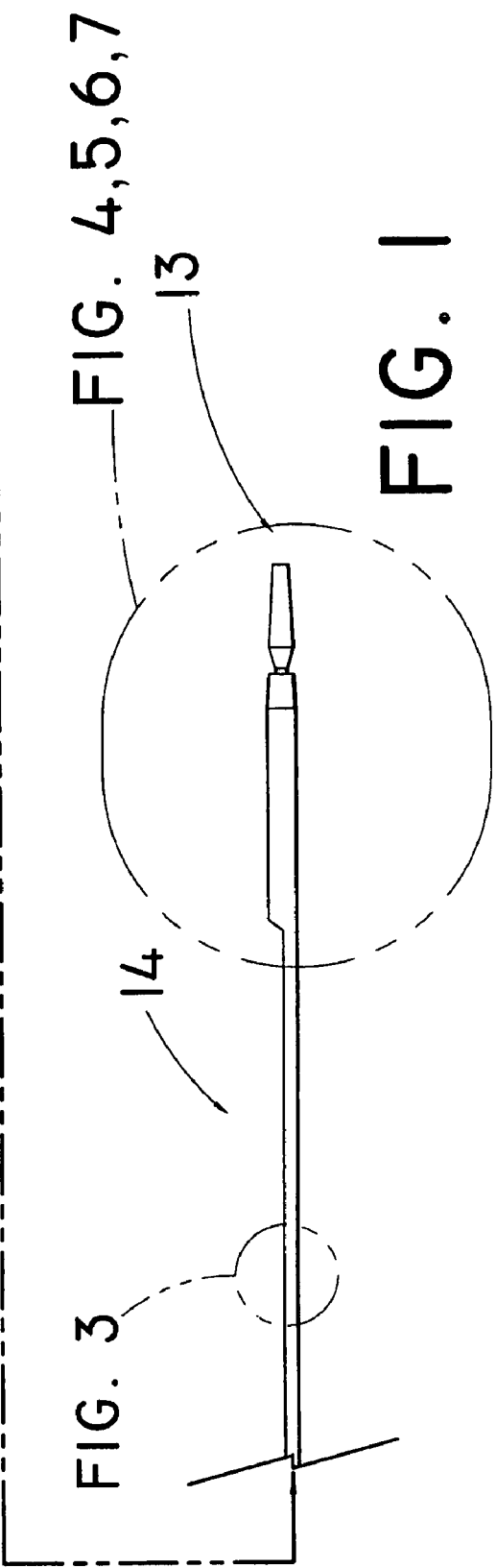

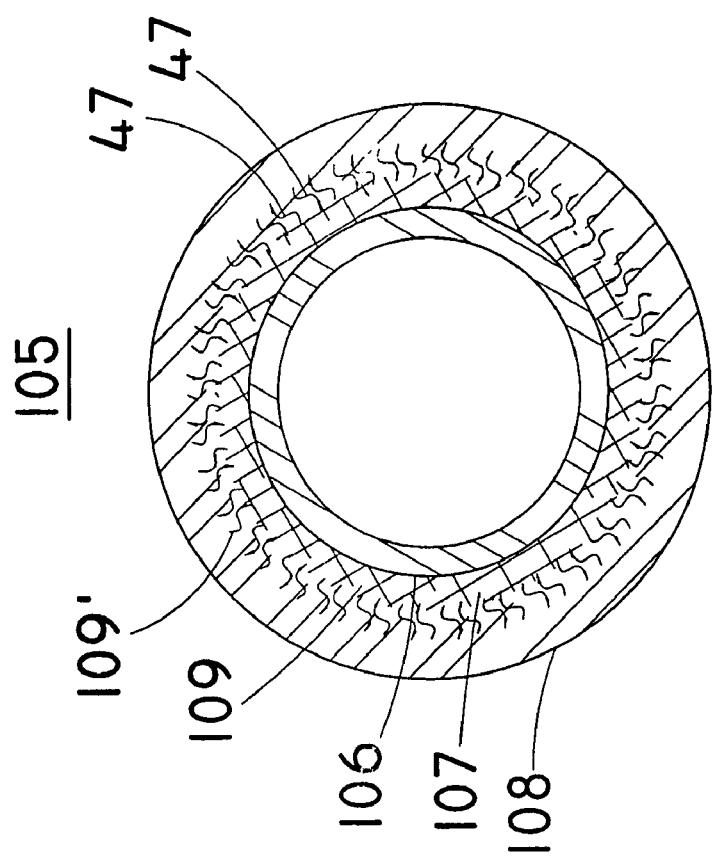
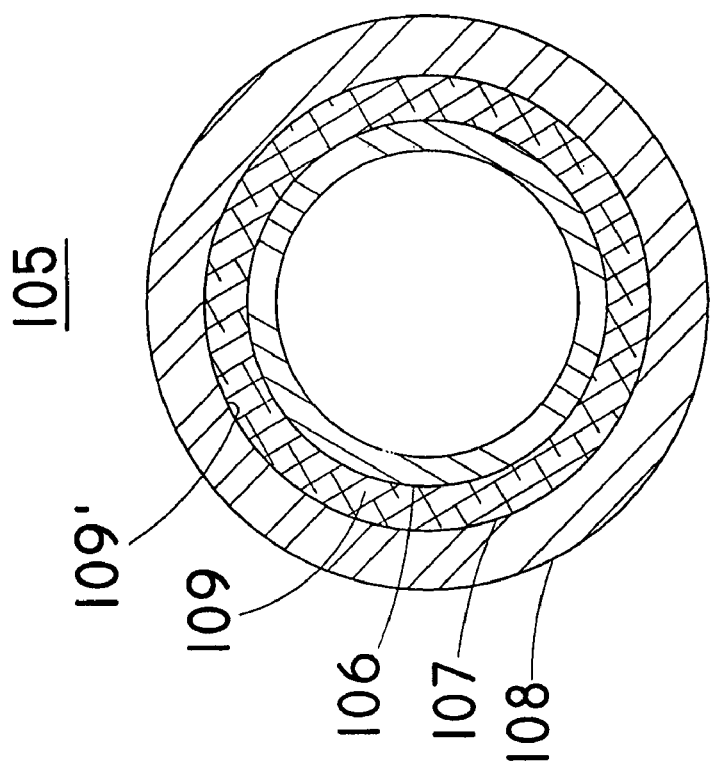
FIG. 4B
FIG. 4A

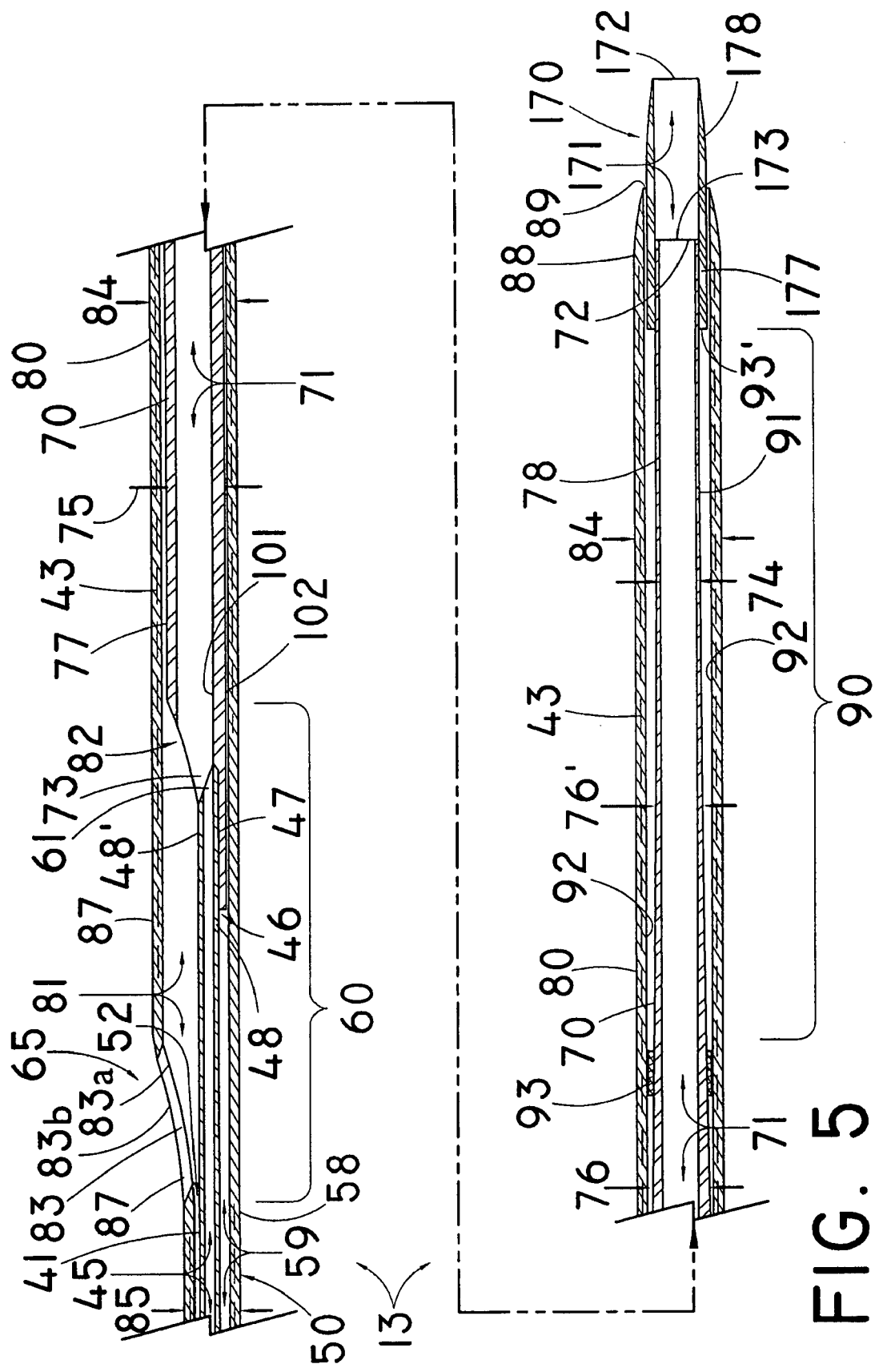

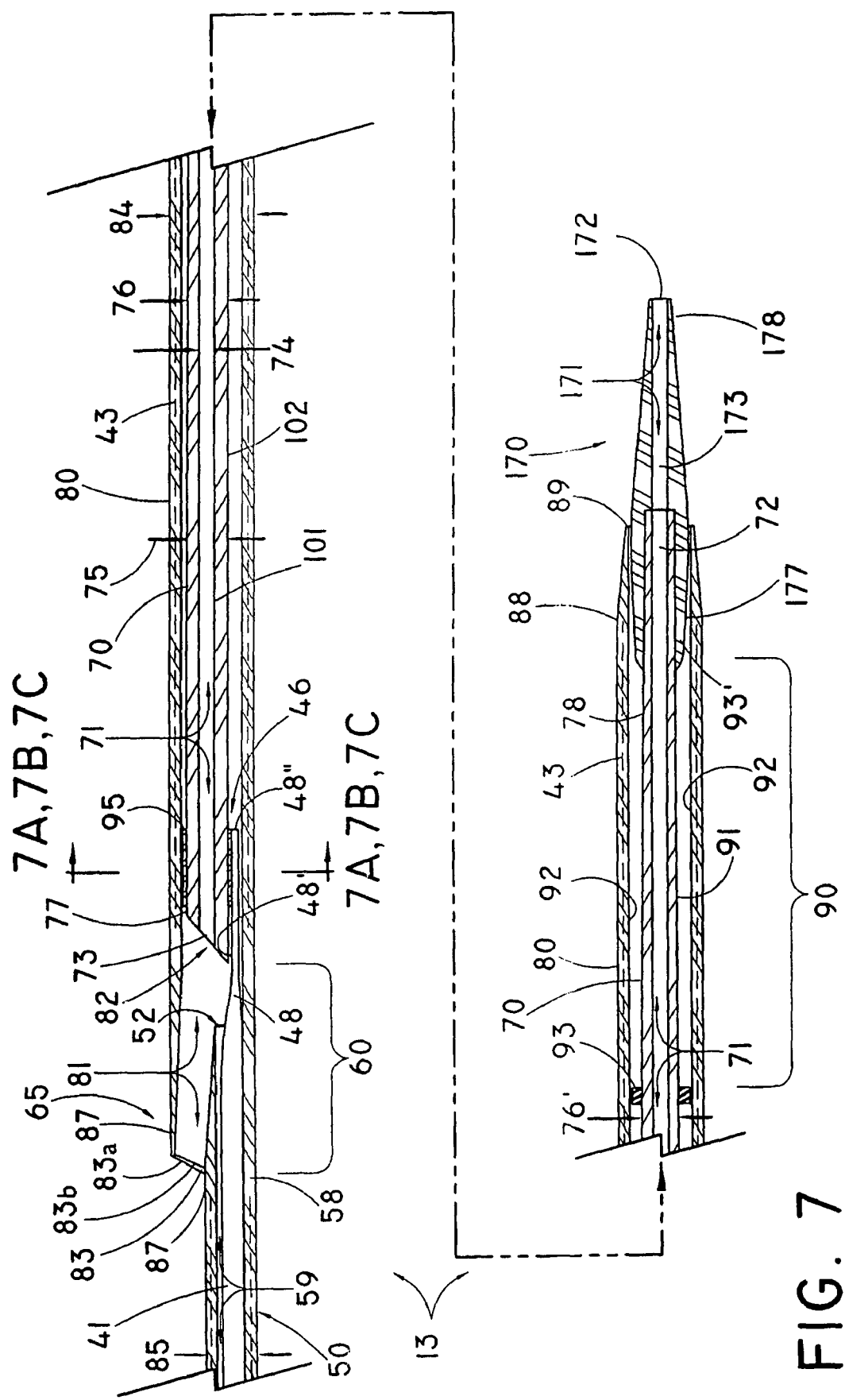

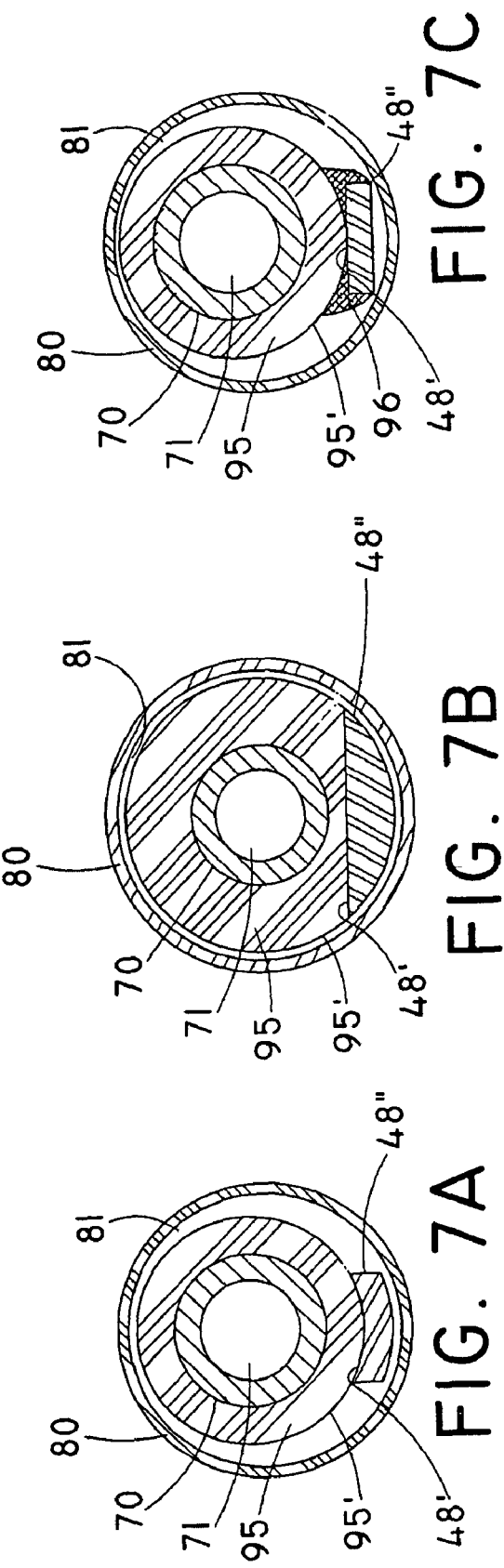

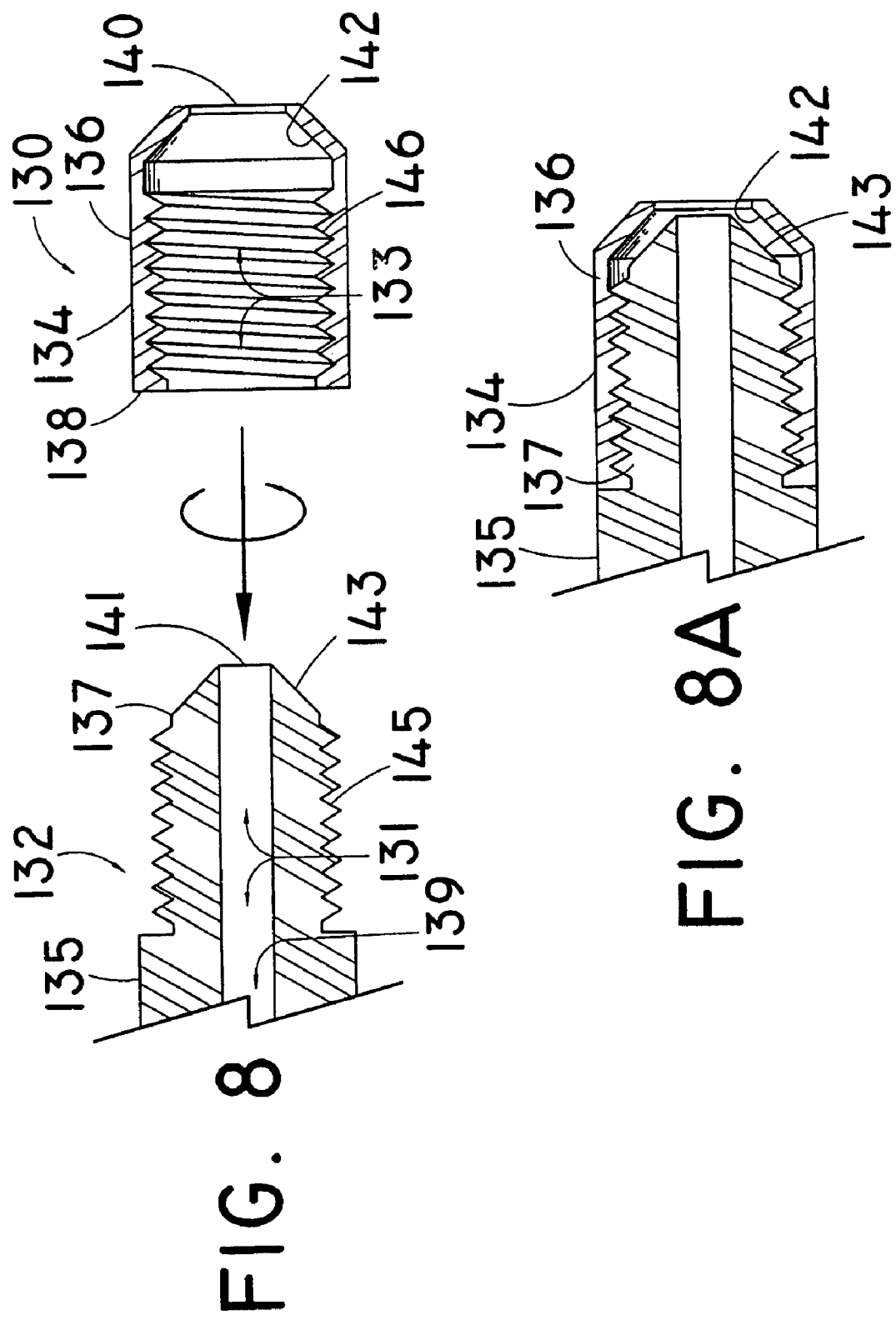

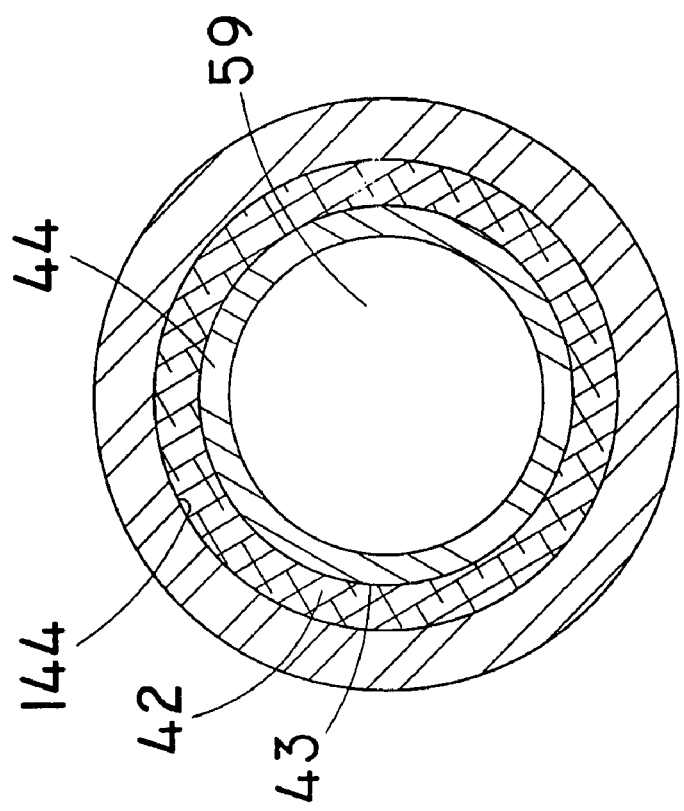
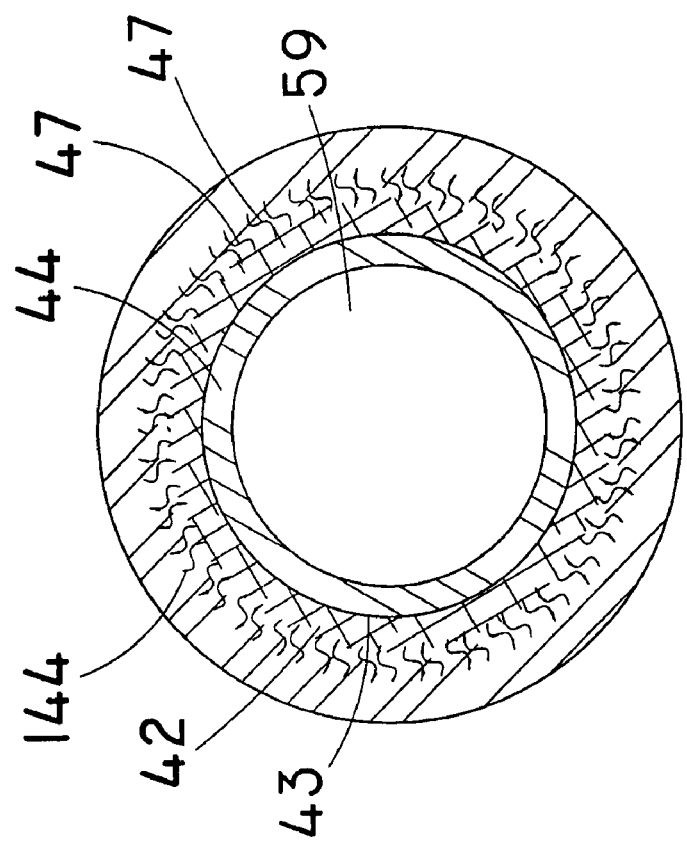

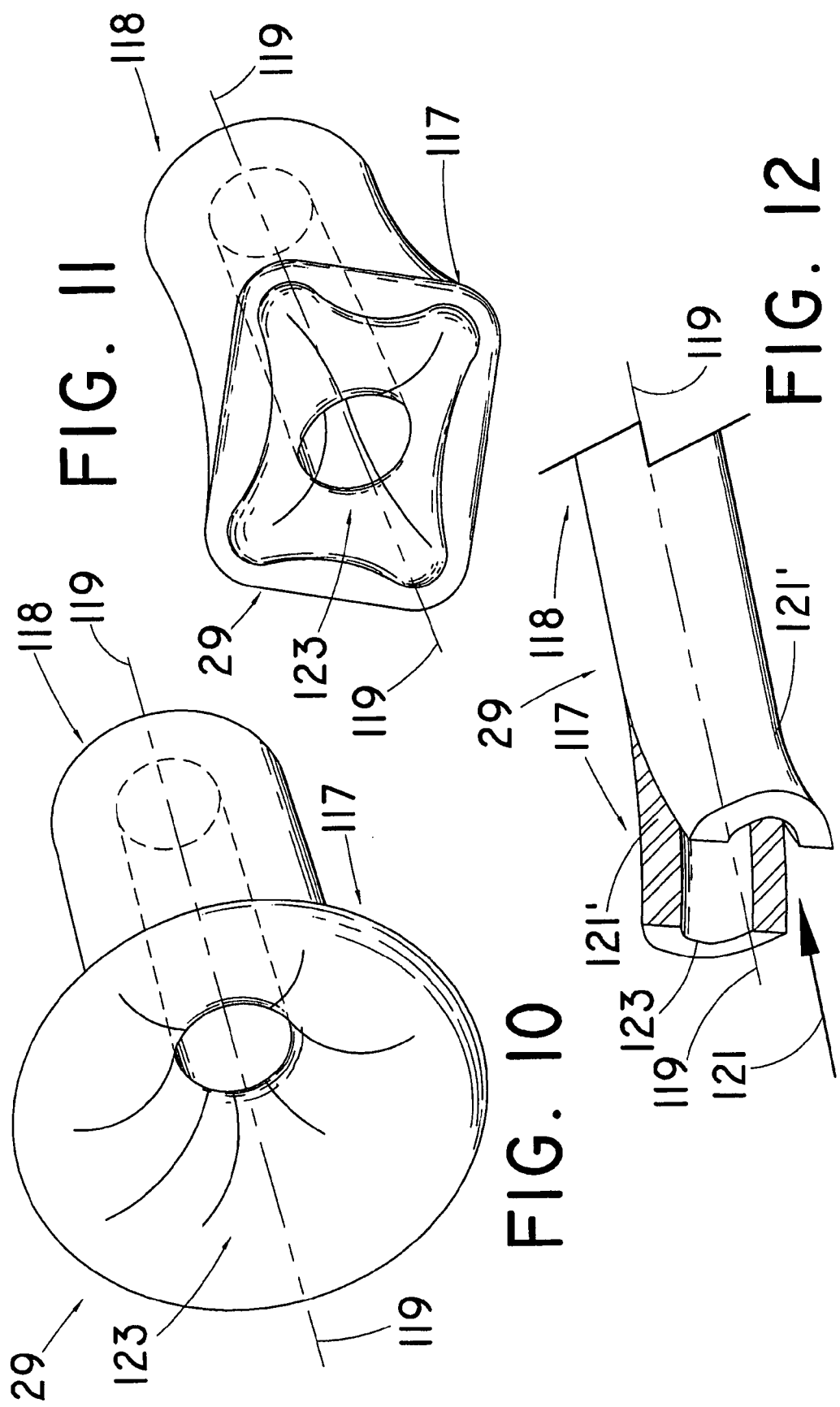

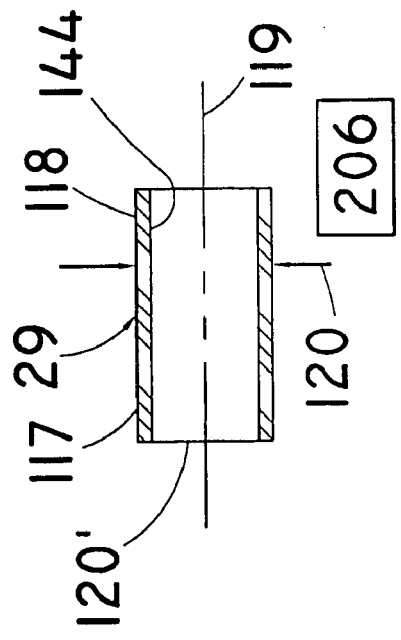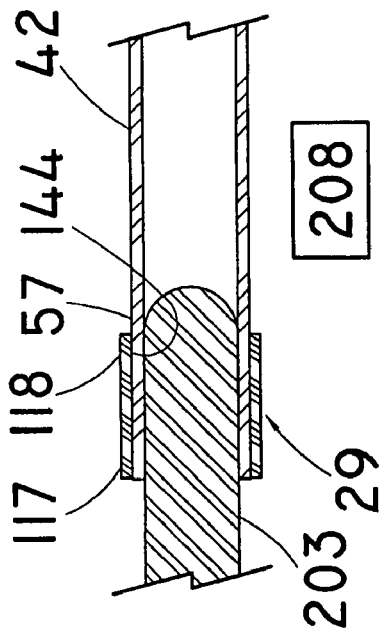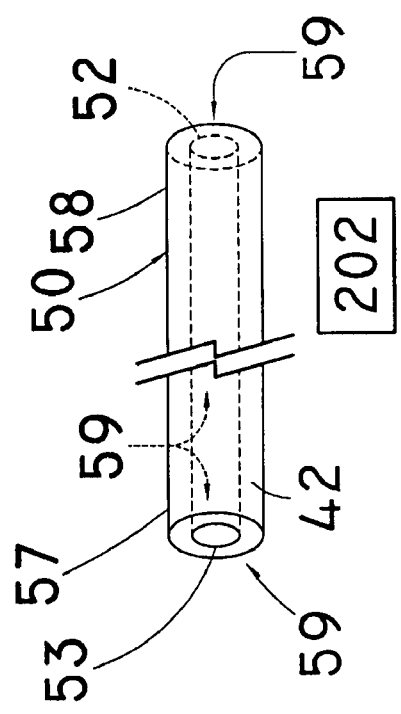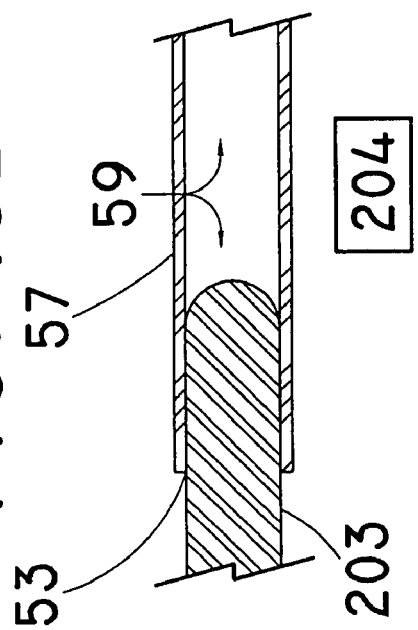

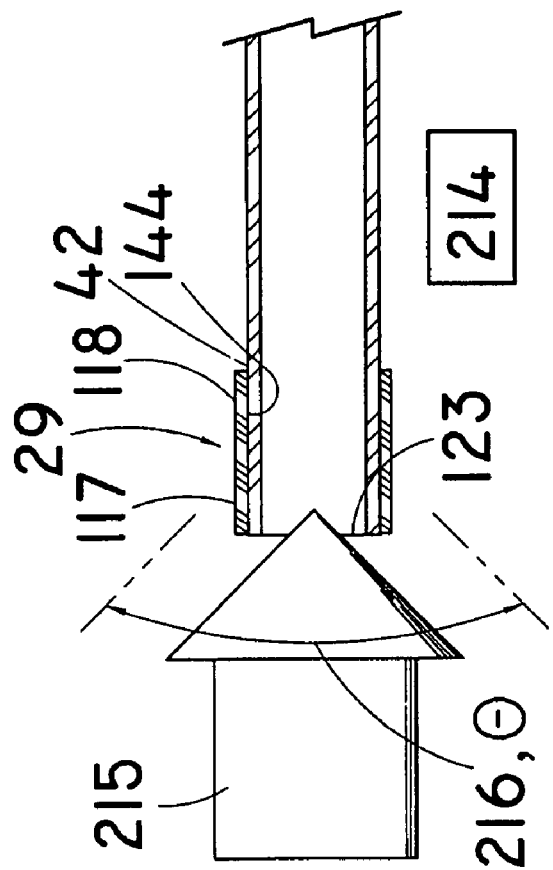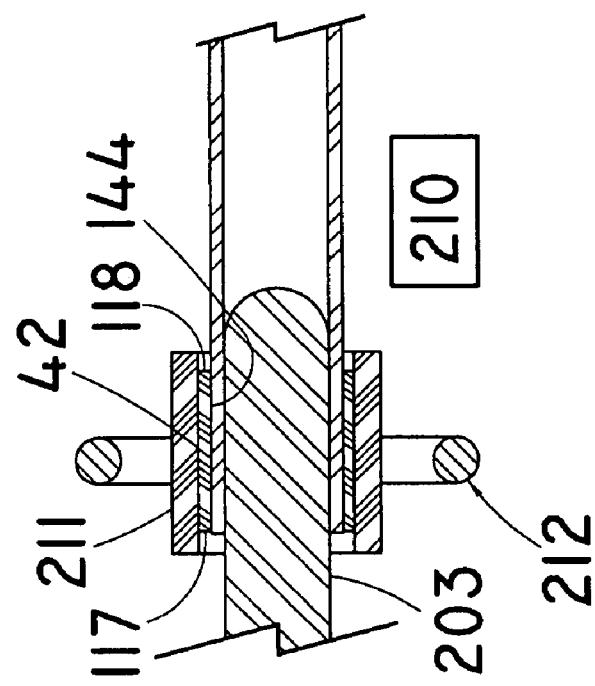

MEDICAL DEVICE DELIVERY SYSTEM HAVING A SHEATH WITH A FLARED STRAIN RELIEF MEMBER OPERATIVELY COUPLED BY A UNIDIRECTIONAL HANDLE

RELATED APPLICATIONS

The present patent document claims the benefit of the filing date under 35 U.S.C. §119(e) of Provisional U.S. Patent Application Ser. No. 60/793,709, filed on Apr. 20, 2006, which is hereby incorporated by reference.

TECHNICAL FIELD

The present disclosure relates generally to medical device delivery systems. More particularly, the invention relates to a strain relief member for use with medical devices that deploy an implantable prosthesis (e.g., a self-expanding, balloon expandable, or non-expanding stent; prosthetic valve devices, and other implantable articles) at a selected location inside a patient's body.

BACKGROUND

This disclosure relates generally to medical device delivery systems, and in particular, to a flared strain relief member disposed about a proximal end portion of an elongate sheath. More particularly, the disclosure relates to a flared strain relief member operatively coupled to a medical device delivery system that employs a unidirectional handle. These systems have a host of uses, including for example, the deployment of rapid insertion self-expanding devices such as stents, prosthetic valve devices, and other implantable articles inside a patient's body (individually and collectively, "stent" or "stents"). Exemplary embodiments of medical device delivery systems have been described in the U.S. Provisional Patent Application filed on Apr. 20, 2005 entitled, "Delivery System and Devices for the Rapid Insertion of Self-Expanding Devices" and having an application Ser. No. 60/673,199, and the non-provisional application filed on Apr. 20, 2006 by the same title and claiming the benefit of the filing date application Ser. No. 60/673,199 under 35 U.S.C. §119(e), the disclosures of which are incorporated in its entirety. The strain relief member may also be used, however, with balloon expandable and non-expanding stents. In addition to being used with a rapid insertion delivery system, the strain relief member may be used in an "over-the-wire" delivery system, so both systems will be described below.

By way of background, stents are configured to be implanted into body vessels having a passageway in order to reinforce, support, repair, or otherwise enhance the performance of the passageway. The term "passageway" is understood to be any lumen, channel, flow passage, duct, chamber, opening, bore, orifice, or cavity for the conveyance, regulation, flow, or movement of bodily fluids and/or gases of an animal. As an example, stents have been used in the passageways of an aorta, artery, bile duct, blood vessel, bronchiole, capillary, esophagus, fallopian tube, heart, intestine, trachea, ureter, urethra, vein, and other locations in a body (collectively, "vessel") to name a few.

One type of stent is self-expanding. For a self-expanding stent, the stent is resiliently compressed into a collapsed first, smaller diameter, carried by the delivery system, and due to its construction and material properties, the stent expands to its second, larger diameter upon deployment. In its expanded configuration, the stent exhibits sufficient stiffness so that it will remain substantially expanded and exert a radially outward force in the vessel passageway on an interior surface of the vessel. One particularly useful self-expanding stent is the Z-stent, introduced by Cook Incorporated, due to its ease of manufacturing, high radial force, and self-expanding properties. Examples of the Z-stent are found in U.S. Pat. Nos. 4,580,568; 5,035,706; 5,282,824; 5,507,771; and 5,720,776, the disclosures of which are incorporated in their entirety. The Zilver stent is another particularly useful self-expanding stent is the Z-stent, introduced by Cook Incorporated, due to its nitinol platform and use of the Z-stent design properties. Examples of the Zilver stent are found in U.S. Pat. Nos. 6,743,252 and 6,299,635 by way of illustration and not by way of limitation, the disclosures of which are incorporated in their entirety.

Many delivery systems employ a tubular catheter, sheath, cannula, introducer, or other medical delivery device (individually and collectively, "catheter") having first and second ends and comprising a lumen for receiving the wire guide. Optionally, these delivery systems may fit through a working channel within an endoscope or an external accessory channel device used with an endoscope.

Generally stated, these delivery systems may fall within two categories. The first category of delivery systems to have been used, and consequently the first to be discussed below, is commonly referred to as an "over-the-wire" system. The other category of delivery systems is sometimes referred to as a "rapid exchange" catheter. In either system, a wire guide is used to position the stent delivery system within a vessel passageway. The typical wire guide has proximal and distal ends. A physician inserts the distal end into the vessel passageway, advances, and maneuvers the wire guide until the distal end reaches its desired position within the vessel passageway.

In the "over-the-wire" catheter delivery system, a physician places the catheter over the wire guide, with the wire guide being received into a lumen that extends substantially through the entire length of the catheter. In this over-the-wire type of delivery system, the wire guide may be back-loaded or front-loaded into the catheter. In front-loading an over-the-wire catheter delivery system, the physician inserts the distal end of the wire guide into the catheter's lumen at or near the catheter's proximal end. In back-loading an over-the-wire catheter delivery system, the physician inserts a distal portion of the catheter over the proximal end of the wire guide. The back-loading technique is more common when the physician has already placed the wire guide into the patient, which is typically the case today. In either case of back-loading or front-loading an over-the-wire catheter delivery system, the proximal and distal portions of the catheter will generally envelop the length of the wire guide that lies between the catheter first and second ends. While the wire guide is held stationary, the physician may maneuver the catheter through the vessel passageway to a target site at which the physician is performing or intends to perform a treatment, diagnostic, or other medical procedure.

Unlike the over-the-wire system where the wire guide lies within the catheter lumen and extends substantially the entire length of the catheter, in a "rapid exchange" catheter delivery system the wire guide occupies a catheter lumen extending only through a distal segment of the catheter. The so-called rapid exchange system comprises a system proximal portion, an elongate flexible middle section delivery device, and a system distal portion that is generally tubular.

The system distal portion, in general, comprises an inner guide channel member sized to fit slidably within an outer guide channel member that is substantially axially slideable relative to the inner member. The outer guide channel member and inner guide channel member further have entry and exit ports defining channels configured to receive a wire guide. A port includes any structure that functions as a portal, port, passage, passageway, opening, hole, cutout, orifice, or aperture, while a guide channel is understood to be any passageway, lumen, channel, flow passage, duct, chamber, opening, bore, orifice, aperture, or cavity that facilitates the passage, conveyance, ventilation, flow, movement, blockage, evacuation, or regulation of fluids or gases or the passage of a diagnostic, monitoring, scope, other instrument, or more particularly a catheter or wire guide.

A wire guide may extend from the outer and inner member entry ports, through the outer and inner member guide channels, and exit the system distal portion at or near a breech position opening located at or near a transition region where the guide channels and exit ports are approximately aligned relatively coaxially to facilitate a smooth transition of the wire guide. Furthermore, the outer guide channel member has a slightly stepped profile, whereby the outer guide channel member comprises a first outer diameter and a second smaller outer diameter proximal to the first outer diameter and located at or near the transition region.

The system distal portion also has a self-expanding deployment device mounting region (e.g., a stent mounting region) positioned intermediate the inner guide channel member entry and exit ports for releasably securing a stent. At the stent mounting region, a stent is releasably positioned axially intermediate distal and proximal restraint markers and sandwiched transversely (i.e., compressed) between the outside surface of the inner guide channel member and the inside surface of an outer guide channel member.

Turning to the system proximal portion of the rapid exchange delivery system, the system proximal portion, in general, comprises a handle portion. The handle portion has a handle that the physician grips and a pusher stylet that passes through the handle. The pusher stylet is in communication with—directly or indirectly through intervening parts—the inner guide channel member at the distal end. Meanwhile, the handle is in communication with—directly or indirectly through intervening parts—the outer guide channel member at the system distal portion. Holding the pusher stylet relatively stationary (while, for example, actuating the handle) keeps the stent mounting region of the inner guide channel member properly positioned at the desired deployment site. At the same time, proximally retracting the handle results in a corresponding proximal movement of the outer guide channel member relative to the inner guide channel member to thereby expose and, ultimately, deploy the self-expanding stent from the stent mounting region. At times, a physician may need to deploy a second self-expanding stent by withdrawing the system from the proximal end of the wire guide. The physician may then reload the catheter with additional stents, and if that is not an option the physician may load another stent delivery system with an additional stent, onto the wire guide. Also, the physician may withdraw the stent delivery system altogether and replace the delivery system with a catheter or different medical device intended to be loaded onto the wire guide.

The delivery system in the rapid exchange delivery system further comprises an elongate flexible middle section delivery device extending intermediate the system proximal portion and the system distal portion. The middle section delivery device comprises an outer sheath and an inner compression member having a first end and a second end portion associated with the system distal portion and system proximal portion, respectively.

More particularly, an outer sheath first end portion may be coterminous with or, if separate from, may be associated with (e.g., joined or connected directly or indirectly) the system distal portion outer guide channel member at or near the transition region, while the outer sheath second end portion is associated with the handle at the proximal end. The inner compression member first end portion is associated with the system distal portion inner guide channel member at or near the transition region, while the inner compression member second end is associated with the pusher stylet at the proximal end. Therefore, the outer guide channel member of the system distal portion may move axially (as described above) and independently relative to an approximately stationary inner guide channel member of the system distal portion and, thereby, deploy the stent.

A challenge in designing the system proximal portion of a delivery system in the rapid exchange delivery system is that the system proximal portion of a catheter for use with the system typically has a small outer diameter that does not mate properly to the handle. The handle could be reconfigured to the smaller physical dimensions of the catheter, but this requires retooling the handle and thereby increasing the manufacturing cost of the delivery system.

Another problem is that the delivery system is continually pulled, twisted, and flexed such that the outer catheter proximal end portion and the handle experience a great deal of force as the delivery system negotiates a tortuous path within a vessel passageway and pulls the outer sheath and/or other stent-covering catheter proximally over the stent in order to expose and thereby to deploy the stent during the medical procedure. Conventional methods of joining strain relief in medical devices may be to use purely mechanical connectors such as lap joints, nuts, pins, screws, clamps, and bushings. Given the small physical dimensions of the catheter and the strain relief, mechanical connectors increase the difficulty in manufacturability and, therefore, the assembly time. Another drawback to a mechanical connector is the propensity to lose the friction fit between the components. Accordingly, a glued joint is often employed as an alternative to a mechanical connector in medical devices. While glue, adhesives, and the like (collectively, "glue"), offer advantages over a mechanical connectors, one must choose the right glue to join dissimilar materials. Also, glue must cure, thereby increasing the total processing (fixture) time in the application and assembly of a joint. In any event, mechanical connectors and glue may vary in strength and integrity depending on the type of materials being joined, and whether the materials have incongruous mating surfaces.

Still another problem in conventional strain relief having a substantially uniform outer diameter is that the attachment point between the strain relief and the handle could dislodge, loosen, or fail due to inadequate stress distribution. When the connection between the strain relief and the handle fails totally or even in part, fluid leakage may result during flushing of the medical device, bodily fluid may leak by a capillary effect, or an air embolism might result. Thus, an improved seal is needed between the strain relief and the handle.

Therefore, it would be desirable to have a strain relief member that solves the aforementioned problems for use in medical device delivery systems such as, for example, a delivery system for deploying an implantable prosthesis (e.g., a self-expanding, balloon expandable, or non-expanding stent; prosthetic valve devices, and other implantable articles) at a selected location inside a patient's body, as taught herein.

SUMMARY

Described herein is a strain relief member for medical devices. In one embodiment, an elongate outer sheath has proximal and distal end portions defining a passageway. A strain relief member has a first end portion disposed about and melt bonded to the outer sheath proximal end portion, and has a flared second end portion with an opening in fluid communication with the outer sheath passageway.

A medical device delivery system for deploying an implantable prosthesis (e.g., a self-expanding, balloon expandable, or non-expanding stent; prosthetic valve devices, and other implantable articles) at a selected location inside a patient's body is described. According to one embodiment, the device includes an elongate outer sheath having a proximal end portion and a passageway. A flared strain relief member has a first end portion operatively coupled to the outer sheath proximal end and having an outer diameter. The flared strain relief member further includes a second end portion having an opening in fluid communication with the outer sheath passageway and having an outer diameter larger than the first end portion outer diameter. A handle has first and second connectors that operatively couple the flared strain relief member second end portion, and the handle second connector has a lumen in fluid communication with the outer sheath passageway.

A method of making a flared strain relief member for a medical device delivery system is also described herein. According to one embodiment, an elongate outer sheath is provided that includes proximal and distal end portions defining a passageway, the proximal end portion having an opening. A mandrel is positioned within the outer sheath proximal end portion opening. A strain relief member is provided, the strain relief member having a first end portion, a second end portion, and defining a lumen therebetween. At least a portion of the strain relief member is disposed about the outer sheath proximal end. A shrink material is disposed about at least a portion of the strain relief member disposed about the outer sheath proximal end portion. Heat is applied to melt bond the strain relief member and outer sheath proximal end portion.

BRIEF DESCRIPTION OF THE DRAWINGS

FIG. 1 is a schematic view, broken away, of a medical device system according to one embodiment.

FIGS. 4A and 4B schematically represent cross sectional views of melt bonding according to one embodiment, where FIG. 4A shows components before melt bonding and FIG. 4B shows the components after melt bonding.

FIG. 5 is a longitudinally sectioned view, broken away, of an alternative embodiment of a distal portion of a medical device delivery system.

FIG. 7 is a longitudinally sectioned view, broken away, of another embodiment of a distal portion of a medical device delivery system.

FIGS. 7A, 7B, and 7C show cross sectional views of FIG. 7 taken along the lines 7A-7A, 7B-7B, and 7C-7C, respectively.

FIGS. 8 and 8A show longitudinally sectioned side views of a handle first connector and a handle second connector according to one embodiment.

FIGS. 9A and 9B show cross sectional views of FIG. 9 taken along the lines 9A-9A and 9B-9B before and after melt bonding according to one embodiment.

FIGS. 10, 11, and 12 show alternative embodiments of a flared strain relief member.

FIGS. 13A through 13F are schematic diagrams illustrating a method of making a flared strain relief member operatively coupled to a proximal end portion of an outer sheath according to one embodiment.

DETAILED DESCRIPTION OF EMBODIMENTS

Figure 2:
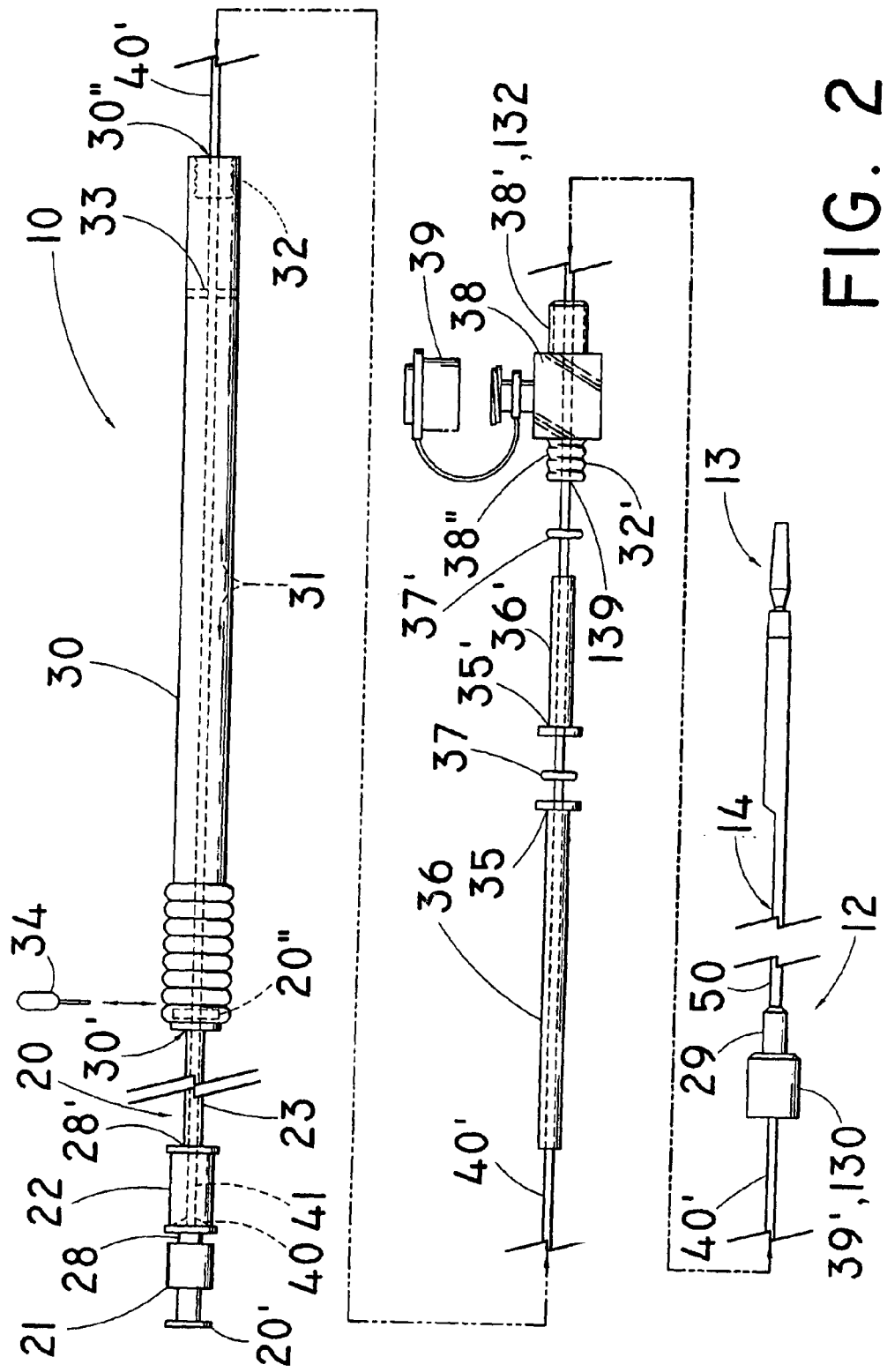
FIG. 2 is an exploded side view, broken away, of a system proximal portion of a medical device according to one embodiment.

The present disclosure relates to medical devices, and in particular to a flared strain relief member for use in a delivery system configured for rapid insertion delivery of self-expanding, non-expanding, and balloon expandable metallic, polymeric, and plastic devices, which devices may include, by way of example and not by way of limitation, stents, prosthetic valve devices, and other implantable articles inside a patient's body. For conciseness and ease of description of the embodiments of the invention, the term "stent" and its variations shall refer individually and collectively (without limiting the invention) to all self-expanding, non-expanding, and balloon expandable devices used with the invention, such as stents, prosthetic valve devices, and other implantable articles inside a patient's body.

For the purposes of promoting an understanding of the principles of the invention, the following provides a detailed description of embodiments of the invention as illustrated by the drawings as well as the language used herein to describe the aspects of the invention. The description is not intended to limit the invention in any manner, but rather serves to enable those skilled in the art to make and use the invention. As used herein the terms comprise(s), include(s), having, has, with, contain(s) and the variants thereof are intended to be open ended transitional phrases, terms, or words that do not preclude the possibility of additional steps or structure.

In FIG. 1, an illustrative embodiment of a delivery system 10 having a host of uses, including for the rapid insertion of self-expanding stents, is provided. The delivery system 10 comprises a system proximal portion 12, a middle section delivery device 14, and a system distal portion 13 shown in a partially deploying position.

System Proximal Portion 12

In the embodiment shown in FIG. 1, the system proximal portion 12 remains outside of the patient's body. The system proximal portion 12 comprises a handle 30 and an optional pusher stylet 20.

FIG. 1 depicts a schematic representation of the handle 30 and the optional pusher stylet 20 shown more particularly in FIGS. 2 and 2A. In general, a handle 30 retracts an outer guide channel member (discussed below) of the system distal portion 13 of the delivery system 10 to deploy a stent, as will be explained later. The handle 30 may comprise any mechanical, electromechanical, pneumatic, or hydraulic handle configured in communication with—directly or indirectly through intervening parts—the distal end's outer guide channel member. Communication would include, by way of illustration and not by way of limitation, a handle 30 that uses or is otherwise associated with, directly or indirectly, an elongated mechanical wire, rod, shaft, cable, sheath, pneumatic tube, or hydraulic pistons, cylinders and/or flow paths configured for moving the outer guide channel member proximally in order to deploy a stent.

FIG. 2 provides a schematic view, broken away, of a delivery system 10 for rapid insertion of self-expanding stents, but could be used with other implantable prostheses described above. The delivery system 10 shown in FIG. 2 is one embodiment of the system proximal portion 12, middle section delivery device 14, and system distal portion 13 shown in a partially deploying position. The middle section delivery device 14 extends distally from the system proximal portion 12, and a system distal portion 13 extends to a position that is distal the middle section delivery device 14. More particularly, FIG. 2 shows an exploded view of the system proximal portion 12 of the delivery system 10 according to one embodiment, with an emphasis on the handle 30 and the optional stylet 20. Against this backdrop, features of one embodiment of a handle 30 and pusher stylet 20 are discussed below.

The handle 30 comprises any tubular structure having a distal aperture 30" and a proximal aperture 30', the apertures defining a chamber 31 therebetween. In general, the handle 30 is a component, instrument, mechanism, tool, device, apparatus, or machine configured for directly or indirectly retracting an outer guide channel member (discussed below) of the system distal portion 13 of the device to expose and, ultimately, to deploy self-expanding implantable prostheses (e.g., stents, prosthetic valve devices, and other implantable articles) at a selected location inside a patient's body.

The handle 30 is axially slideable relative to an elongate (long) inner compression member 41 that comprises a proximal end 40 and a middle section 40'. As discussed more fully below, the inner compression member 41 helps to keep the stent from moving proximally with proximal movement of the handle 30, which handle movement causes the outer guide channel member to withdraw proximally over the stent in order to expose and thereby to deploy the stent. Thus, the inner compression member helps to "push" the stent or stent carrying inner guide channel member in order to counter the urge for the stent or stent carrying member to prolapse proximally with the withdrawing of the outer guide channel member. As will be understood, "pushing" on the inner compression member will keep the stent carrying inner guide channel member (and therefore the stent) from translating as a result of an outer sheath or outer guide channel member being pulled over the stent; thereby "pushing" holds the stent in place at the desired deployment site within the patient's body. In one embodiment, the handle 30 is a unidirectional handle that is axially slideable relative to the inner compression member 41 and/or the optional pusher stylet 20 in order to deploy a stent. In one embodiment, the inner compression member 41 is secured to a pusher stylet 20.

As shown in FIG. 2, one embodiment of a pusher stylet 20 comprises a proximal end 20', a distal end 20", and a cannula 23 intermediate the proximal and distal ends 20', 20", respectively, and a receptacle 22. The cannula 23, as should be understood, comprises any suitable hollow plastic or metal tube. As a hollow tube, the cannula 23 optionally allows the inner compression member 41 to pass proximally through the cannula 23 and to the proximal end 20' so that the inner compression member proximal end 40 (such as a flared proximal end 40) may secure to a plug 21 that fits within the receptacle 22, wherein FIG. 2 shows the proximal end 20', plug 21, and an optional securing material 28 are shown in an exploded view relative to the receptacle 22 into which they may be secured. Furthermore, the cannula 23 assists with keeping that portion of the inner compression member substantially straight.

The stylet 20 is optional, because in an alternative embodiment the physician may hold the inner compression member proximal end 40' directly in order to "push" (e.g., hold substantially stationary) the stent carrying inner guide channel member (and therefore the stent). This controls the stent carrying inner guide channel member and stent from translating as a result of an outer sheath or outer guide channel member being pulled over the stent, so that the stent remains at the desired deployment site within the patient's body. Alternatively, the stylet 20 is any stationary handle secured to the inner compression member 41 for achieving the "pushing" (e.g., hold substantially stationary) of the stent or stent carrying inner guide channel member while the outer sheath or outer guide channel member are moved proximally.

The stylet distal end 20" is housed within the handle chamber 31 and is flared or otherwise flanged sufficiently to be larger than the handle proximal aperture 30' so as not to pull out of the chamber 31. In one embodiment, the stylet distal end 20" is secured to the distal portion of the stylet cannula 23, while in another embodiment the stylet distal end 20" is formed integral with the distal portion of the stylet cannula 23. Consequently, the stylet distal end 20" functions as a proximal stop that prevents the stylet cannula 23 from backing all the way out the handle while being axially slideable within the handle chamber 31. Thus, the stylet 20 will not slide off the handle 30, if so desired. The stylet distal end 20" may also, in one embodiment, function as a distal stop against a restraint 33 formed in the handle chamber 31 intermediate the handle proximal and distal apertures 30', 30", respectively, where intermediate should be understood to be any position between, and not necessarily equidistant to, the handle apertures 30', 30". As a result of the stylet distal end 20", the handle 30 may slide axially the distance separating the handle restraint 33 and the stylet distal end 20", which has a maximum distance of when the stylet distal end 20" is abutting the handle proximal aperture 30'.

A threaded tapered plug 21 and threaded tapered receptacle 22 optionally secure the inner compression member proximal end 40. In one embodiment, the inner compression member proximal end 40 is flared. Securing material 28, such as glue, adhesives, resins, welding, soldering, brazing, chemical bonding materials or combinations thereof and the like (collectively and individually, "glue") may be used to keep the threaded tapered plug 21 from backing out of the threaded tapered receptacle 22. A portion of the cannula 23 and stylet distal end 20" are received within the handle chamber 31 distal to the handle proximal aperture 30' as previously explained.

By optionally placing the inner compression member proximal end 40 in mechanical communication with the plug 21 and receptacle 22, the gripping and "pushing" (e.g., hold substantially stationary) on the stylet 20 (e.g., the receptacle 22) thereby helps to keep the inner compression member 41 from moving away from the system distal portion 13 and, accordingly, counters the tendency for a stent or stent carrying member to move proximally during withdrawal of the outer guide channel member as will be explained below. Of course, the inner compression member may be secured elsewhere by the stylet 20, such as at or near the stylet distal end 20" or intermediate the stylet proximal and distal ends 20',

20", respectively, and the stylet distal end 20" may extend to a position at or near the distal end aperture 30" of the handle 30.

FIG. 2 shows a middle section 40' that extends distally from the proximal end 40 of the inner compression member 41. In one embodiment, the middle section 40' passes through the handle 30 (and may pass through the cannula 23 and/or bushings housed within the handle chamber 31 or other portions of the system proximal portion 12). In one embodiment, the middle section 40' is elongate (at least 50.0 cm or longer as described below) and extends to a distance distally of the handle 30 and to a position at or near the system distal portion 13 of a delivery system 10. It should be understood that, by describing the middle section 40' as passing through the handle 30, the middle section 40' does not necessarily need to pass proximally through the entire length of the handle 30, such as in an embodiment (by way of example and not by way of limitation) where the proximal end 40' of the inner compression member 41 is secured to a distal portion of the cannula 23 and/or the stylet distal end 20" extending within the handle chamber 31 to a position at or near the handle restraint 33.

In addition to holding a threaded tapered plug 21 and optionally the proximal end 40 of the inner compression member 41, the threaded tapered receptacle 22 may secure the proximal portion of the optional cannula 23. Glue 28' may be used at or near an interface of the cannula 23 and distal aperture of the threaded tapered receptacle 22. The glue 28' serves many functions, such as to keep dust from settling within the threaded tapered receptacle 22, to make the cannula 23 easier to clean, and to give aesthetics and a smooth feel to the device.

The handle 30 slidably receives the distal portion of the cannula 23 within the handle aperture 30' and handle chamber 31. As a result, the handle 30 is slidable relative to the stylet 20 (e.g., slidable relative to the threaded tapered plug 21, threaded tapered receptacle 22, and the cannula 23). In use, the physician grips the handle 30 in one hand and grips the stylet 20 (e.g., the receptacle 22) in the other hand. The physician holds the stylet 20 relatively stationary, which prevents the inner compression member and inner guide channel member and its stent carrying portion from moving proximally, and then withdraws the handle 30 proximally relative to the stationary stylet 20 and inner compression member 41. As a result, the physician is thereby retracting an outer guide channel member (discussed below) of the system distal portion 13 of the delivery system 10 to expose and, ultimately, deploy a stent locatable at the system distal portion 13 of the delivery system 10. The handle 30 is in communication with—directly or indirectly through intervening parts—the outer guide channel member at the system distal portion 13.

As shown in FIG. 2, some of those optional parts may include the following: a first bushing 36 having an optional first bushing flange 35; a second bushing 36' having an optional second bushing flange 35'; an intermediate seal 37 intermediate the first and second bushing flanges 35, 35', respectively; a second seal 37' intermediate the second bushing flange 35' and a check flow body 38; and a detachable cap 39, such a Luer cap by way of example but not by way of limitation. In one embodiment, one or both of the intermediate seal 37 and the second seal 37' is from a class such as an O-ring. In another embodiment, one or both of the intermediate seal 37 and the second seal 37' is a cylinder or disk with a center aperture, and may be made from material that comprises an O-ring. The bushings 36, 36' are hollow plastic or metal tubes that take up space within the handle 30 so that the inner compression member has less room to buckle. Fully assembled in one embodiment, the first bushing 36 is inserted within the cannula 23 and the first bushing flange 35 is distal to and abutting the handle restraint 33, which is sized to interfere with the bushing flange 35 to prevent the bushing flange 35 from moving proximal to the handle restraint 33. The second bushing flange 35' is distal to and optionally abutting the bushing flange 35 so to prevent it from moving proximal the first bushing flange 35, and the second bushing 36' is inserted within an opening 139 of the check flow body 38. The intermediate seal 37 and the second seal 37' help to prevent fluids that could be used with the device (discussed below) from entering the handle chamber 31, which directs fluids distally, which fluids may be conveyed through an outer sheath 50 of the middle section delivery device 14 and system distal portion 13. In one embodiment, the handle restraint 33 is from a class such as a counterbore wherein the restraint 33 comprises, by way of example only and not by way of limitation, a flat-bottomed cylindrical enlargement of the handle chamber 31 sized for receiving a first bushing flange 35, an intermediate seal 37, a second bushing flange 35', and/or a check flow body proximal mating end 38" intermediate the restraint 33 and the handle distal aperture 30".

The handle 30 and check flow body 38 operatively couple with the handle distal aperture 30" receiving a check flow body proximal mating end 38" and being secured together by any suitable means, including but not limited to a crimp, friction fit, press fit, wedge, threading engagement, glue, adhesives, resins, welding (laser, spot, etc.), soldering, brazing, adhesives, chemical bonding materials, or combinations thereof an one embodiment, the handle 30 comprises a coupling member 32 and the check flow body proximal mating end 38" comprises a coupling member 32', the coupling members 32, 32' being complementary to hold the handle 30 and check flow body proximal mating end 38" together. In one embodiment, the coupling members 32, 32' may form complementary threads. If it is desired to achieve quicker assembly for manufacturing purposes, then the coupling members 32, 32' may be an array of circumferential ridges that form an interference fit when pressed together. If a one-time snap fit is desired, then the coupling members 32, 32' may be circumferential ridges in the form of barbs. In another embodiment, the handle 30 and check flow body proximal mating end 38" may be put together and taken apart for servicing, in which case the coupling members 32, 32' may be circumferential ridges in the form of knuckle threads (e.g., circumferential ridges forming complementary undulating waves). The operatively coupled handle 30 and check flow body proximal mating end 38" according to these embodiments may be fixed such that they do not rotate relative to each other, or may rotate while preventing undesired axial separation.

During use, the detachable cap 39 may be detached or opened and the device flushed with saline to remove air in order to help keep air out of the patient. The intermediate seal 37 and the second seal 37' ensure that any flushed fluid moves distally in the device and does not back up into the handle 30, such as between the handle restraint 33 and the first bushing 36, into the handle chamber 31, or out the handle proximal aperture 30'. The detachable cap 39 (such as a Luer cap) keeps saline from backing out of the check flow body 38, air from flowing into the check flow body 38, and blood from rushing out during periods of high blood pressure inside the patient.

The medical device delivery systems 10 may be used to deploy an implantable prosthesis that is a balloon expandable or self-expanding stent, prosthetic valve device, or other implantable articles provided on the distal end of a delivery system. In operation, a physician inserts the distal end and at least a portion of the middle section delivery device into a vessel passageway, and advances them through the vessel passageway to the desired location adjacent the target site within the vessel passageway of a patient. In a subsequent step, the physician moves the handle proximally, which withdraws the outer sheath and/or the outer guide channel member and releasably exposes the stent for deployment. In another step, the physician inflates the expandable member, such as a balloon, positioned under the stent inner surface to plastically deform the stent into a substantially permanent expanded condition. The physician may inflate the expandable member by injecting fluid such as saline from a syringe into the inner compression member 41, via pusher stylet 20, through a Luer fitting at the proximal end 20'. Therefore, the fluid is directed distally to the expandable member, filling the expandable member chamber and expanding the stent. The physician then deflates the balloon and removes the catheter or delivery device from the patient's body.

In one embodiment as shown in FIG. 2, the handle 30 further comprises a check flow body distal mating end 38' and a connector cap 39' (optionally detachable) secured to the check flow body distal mating end 38', and a strain relief 29. In one embodiment, the connector cap 39' is from a class of fasteners such as nuts, and in one embodiment is a flare nut. The connector cap 39' functions to hold (or assist in holding in combination with the check flow body distal mating end 38') a flared proximal portion of an outer sheath 50 and/or a flared strain relief 29 disposed about (and optionally extending proximally from) that held portion of the outer sheath 50. The strain relief member 29 provides a kink resistant point where the outer sheath 50 connects to the connector cap 39' and/or the check flow body distal mating end 38'.

The check flow body distal mating end 38' and connector cap 39' may be operatively coupled mechanically, chemically, and/or chemical-mechanically. In one embodiment, the connector cap 39' is crimped, friction fitted, press fitted, and/or wedged into engagement onto the check flow body distal mating end 38'. In another embodiment for example, the check flow body distal mating end 38' and connector cap 39' are operatively coupled by glue, adhesives, resins, welding (laser, spot, etc.), soldering, brazing, adhesives, chemical bonding materials, or combinations thereof.

By way of example only and not by way of limitation, the terms "operatively coupling," "operatively coupled," "coupling," "coupled," and variants thereof are not used lexicographically but instead are used to describe embodiments having a point, position, region, section, area, volume, or configuration at which two or more things are mechanically, chemically, and/or chemical-mechanically bonded, joined, adjoined, connected, associated, united, mated, interlocked, conjoined, fastened, held together, clamped, crimped, friction fit, pinching, teeth, press fit tight, nested, wedged, a joint, a junction, a juncture, a seam, a union, a socket, a melt bond, glue, adhesives, resins, welding (laser, spot, etc.), soldering, brazing, adhesives, chemical bonding materials, implanted, or combinations thereof.

Thus, the check flow body 38 provides an optional three way connector. The check flow body proximal mating end 38" and handle coupling member 32 are operatively coupled. The side port is controlled by the detachable connector cap 39. And the body distal mating end 38' is operatively coupled to a second connector cap 39'.

The foregoing description of a system proximal portion 12 of a medical device delivery system 10 according to one embodiment may be one assembly during shipping, or may include a two-part assembly or more. Otherwise stated, the stylet 20 and handle 30 may be sold already combined or may be combined after purchase by inserting the stylet cannula 23 into the handle at the hospital via the threaded tapered plug 21 and threaded tapered receptacle 22. An optional safety lock 34 helps to ensure against unintentional actuation by preventing distal movement of the stylet distal end 20" by extending inwardly within the handle chamber 30 through a slot in the handle outer wall distal to the handle proximal aperture 30'. Consequently, the optional safety lock 34 thereby maintains the handle 30 in an undeployed position until the physician is ready to deploy an implantable prosthesis (e.g., a self-expanding, balloon expandable, or non-expanding stent; prosthetic valve devices, and other implantable articles) at a selected location inside a patient's body.

Middle Section Delivery Device 14

A delivery system 10 as shown in FIGS. 1 and 2 comprises a middle section delivery device 14. According to one embodiment, the middle section delivery device 14 is intermediate the system proximal portion 12 (FIGS. 1, 2) and the system distal portion 13 (FIGS. 1, 2) of the delivery system 10. The term "intermediate" is intended to describe embodiments whereby the middle section delivery device 14 is intermediary, intervening, lying or occurring between two extremes, or spatially in a middle position, state, or nature—though not necessarily equidistant—between the distal tip of the system distal portion 13 and the proximal tip of the system proximal portion 12. Furthermore, the middle section delivery device 14 may overlap or be partially inserted into a portion of the system distal portion 13 and/or the system proximal portion 12. In another embodiment, a portion of the middle section delivery device 14 (such as the sheath 50 explained below) and the outer guide channel member 80 (discussed below; see FIGS. 4-7) of the system distal portion 13 may be an elongate tubular catheter or Flexors sheath of integral construction.

According to one embodiment, a middle section delivery device 14 is a flexible, elongate (long, at least about 50.0 centimeters ("cm")) tubular assembly. In one embodiment, the middle section delivery device 14 is from approximately 100.0 centimeters ("cm") to approximately 125.0 cm for use when placing a system distal portion 13 of the device within a patient's body, although it may be sized longer or shorter as needed depending on the depth of the target site within the patient's body for delivering the stent. The term "tubular" in describing this embodiment includes any tube-like, cylindrical, elongated, shaft-like, rounded, oblong, or other elongated longitudinal shaft extending between the system proximal portion 12 and the system distal portion 13 and defining a longitudinal axis. As used herein and throughout, the term "longitudinal axis" should be considered to be an approximate lengthwise axis, which may be straight or may at times even be curved because the middle section delivery device 14, for instance, is flexible and the system distal portion 13 also may be substantially or partially flexible.

A middle section delivery device 14 comprises an outer sheath 50. The outer sheath 50 comprises a passageway 59 (e.g., FIGS. 2, 4-7). The middle section delivery device 14 further comprises an elongate inner compression member 41 (e.g., FIGS. 2, 2C, 4-7). The outer sheath passageway 59 is configured for slideably receiving the inner compression member 41, a catheter, or other medical device.

Figure 3:
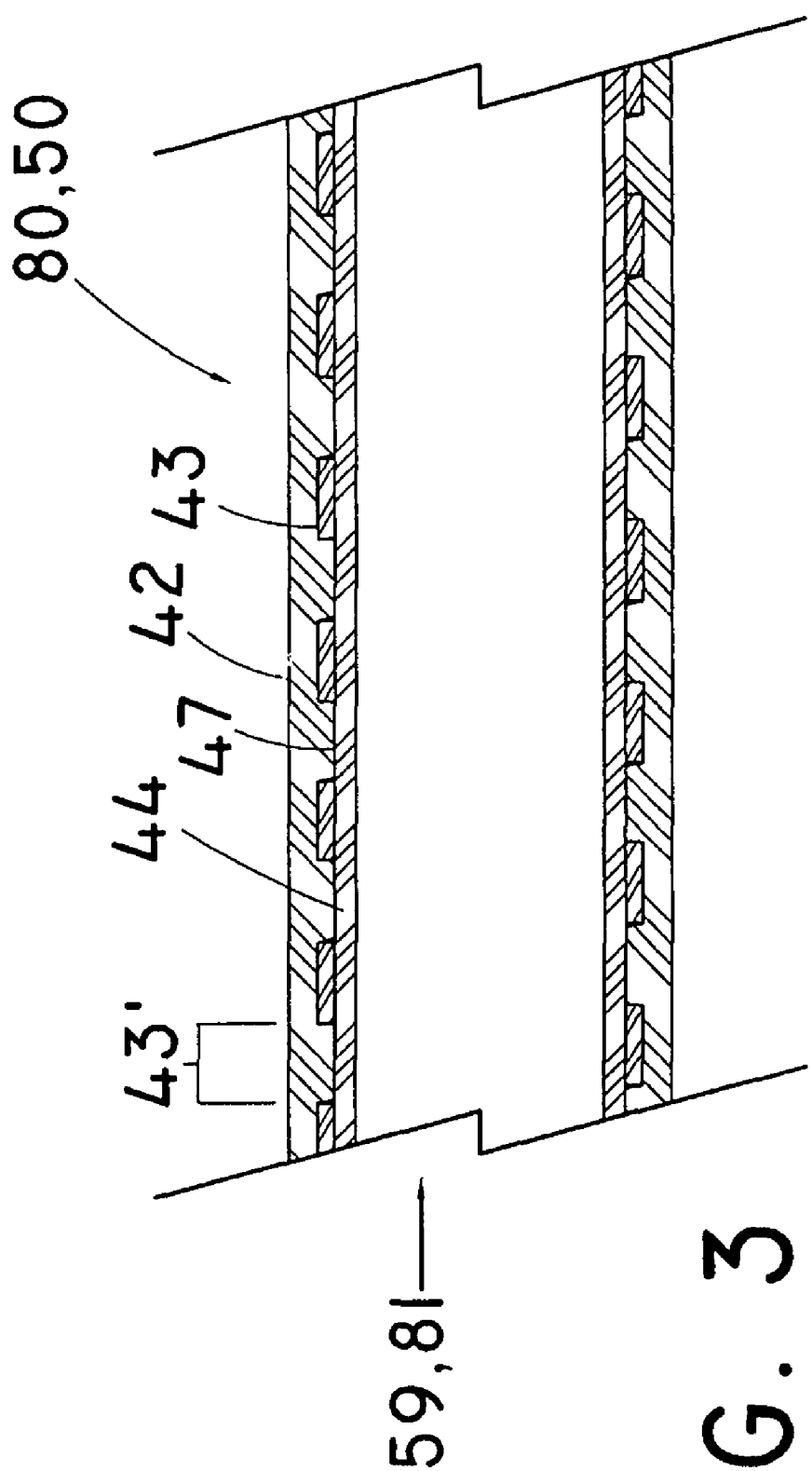
FIG. 3 is a longitudinally sectioned side view of a partial length of a catheter according to one embodiment, where the catheter is used for an outer sheath of a system middle section delivery device and/or for an outer guide channel member of a system distal portion of a medical device.

FIG. 3 depicts an enlarged, longitudinally sectioned view along a partial length of an outer sheath 50 for use as the middle section delivery device 14, with the delivery system's proximal and distal end portions 12, 13, respectively, of the device being removed for clarity. In one embodiment, the outer sheath 50 comprises three layers: an inner layer 44 comprising Teflon material; a middle layer comprising a stainless steel circumferential spiral coil 43; and an outer layer 42 comprising a nylon and/or a polyether block amide ("PEBA"). The outer layer 42 and inner layer 44 optionally may comprise a lubricious material, one example of which includes a fluorocarbon such as polytetrafluoroethylene (PTFE), to present a slideable surface to allow easier inserting and retracting the middle section delivery device 14 for deploying a self-expanding stent, as will be explained later.

The wall of the inner layer 44 of the outer sheath 50 has sufficient radial rigidity to decrease any tendency of bulging, kinking, and the like under an internal radial expansile force. In other words, the inner layer 44 resists an inner object from protruding or becoming embedded into the inner layer 44, which is beneficial to the slideability of an outer sheath 50. The coil 43 may be compression fitted or wound around the inner layer 44. The coil 43 includes a plurality of turns, and preferably includes uniform spacings 43' between the turns of the coil 43. The coil 43 may be formed of any suitable material that will provide appropriate structural reinforcement, such as stainless steel flat wire or biologically compatible metals, polymers, plastics, alloys (including super-elastic alloys), or composite materials that are either biocompatible or capable of being made biocompatible.

Although the embodiment in FIG. 3 shows a flat ribbon shaped wire coil 43, coils of other cross-sectional dimensions, such as round wire, may also be used. When flat wire stainless steel is used, the coil 43 is optionally formed from wire that is about 0.003 inches thick by about 0.012 inches wide. In one embodiment, the turns of coil 43 are uniformly spaced 43' apart by approximately 0.0118 inches. While FIG. 3 shows an embodiment that uses coils 43 having uniformly spaced turns and a constant pitch, this is not required and coils 43 may be spaced 43' by non-uniform distances or at varying distances. In one embodiment, the ends of coil 43 are positioned approximately 0.197 inches proximal to the system distal portion 13 and approximately 0.591 inches distal to the system proximal portion 12.

The outer sheath 50 for use with the middle section delivery device 14, and the outer guide channel member 80 (FIGS. 4-7) and/or the inner guide channel member 70 (FIGS. 4-7) for use with the system distal portion 13, are available for purchase from Cook Incorporated, of Bloomington, Ind. under the trade name of "Flexor®." Examples of the Flexor® sheath devices, materials, and methods of manufacturing them are found in U.S. Pat. Nos. 5,700,253 and 5,380,304, the contents of which are incorporated herein by reference. The Flexor® sheath is particularly suited for the outer sheath 50 of the middle section delivery device 14 and/or the outer guide channel member 80 of the system distal portion 13 due to its thin PTFE liner on the inside wall of the inner layer 44, thin flat wire coil 43, and Nylon and/or PEBA overcoat 42 that captures the coil 43 and PTFE liner 44 and binds the structure together. The PTFE inner layer 44 of the Flexor® sheath resists an expansile inner object from protruding or becoming embedded into the inner layer 44 and, thereby, provides a slick, smooth surface that slides (e.g., across the surface of a stent if the Flexor® sheath is used with the system distal portion 13 or across the surface of an inner compression member 41 if the Flexor® sheath is used with the middle section delivery device 14) relatively easily when retracted to expose, release, and deploy the stent or allow the outer sheath 50 to move relative to the inner compression member 41, and the outer guide channel member 80 to move relative to the inner guide channel member 70, during deployment of the stent.

As an alternative to purchasing the outer sheath 50 for use with the middle section delivery device 14 and the outer guide channel member 80 for use with the system distal portion 13 from Cook Incorporated, one may manufacture the outer sheath and outer guide channel member from various component parts. For instance, one may purchase a tubular inner layer 44 comprising a lubricious material comprising a fluorocarbon such as polytetrafluoroethylene (PTFE or Teflon) from Zeus, Inc. in Orangeburg, S.C., and dispose that inner layer 44 over a mandrel. Alternatively, a sheet of material comprising Teflon may be positioned on a mandrel and formed into a tubular body for the inner layer 44 by any suitable means known to one skilled in the art.

The tubular inner layer 44 (whether formed from a sheet on a mandrel or purchased as a tube and slid onto a mandrel) may be slightly longer than the desired length described above for the outer sheath 50 and/or outer guide channel member 80, and slightly longer than the mandrel. In one embodiment, the tubular inner layer 44 may extend about 5.0 cm from each mandrel end. As explained below, the "loose" ends of the tubular inner layer 44 help during manufacturing of the device.

The mandrel-tubular inner layer 44 assembly is prepared for a middle layer comprising a stainless steel circumferential spiral coil 43 as described above and available for purchase from Cook Incorporated or Sabin Corporation in Bloomington, Ind. As purchased, the coil 43 comes in a long, pre-coiled configuration and will be cut by hand or machine to the desired length either before or after winding the coil about the inner layer 44 to the desired length. As an alternative, one may manufacture the coil from raw material available from Fort Wayne Medical in Fort Wayne, Ind., and process it into a spiral coil 43 shape.

The operator may apply the spiral coil 43 about the mandrel-tubular inner layer 44 assembly by hand or machine. If by hand, then an end of the spiral coil 43 may be started onto the tubular inner layer 44 by any suitable means, for example, such as hooking and winding (e.g., wrapping) the coil 43 around the tubular inner layer 44 in a pigtailed manner at an initial position a desired distance (e.g., 5.0 cm or more) from a first end of the tubular inner layer 44 and to a terminating position that is a desired distance (e.g., 5.0 cm or more) from a second end of the tubular inner layer 44, and then cutting the coil 43 at the terminating position before or after hooking the coil 43 onto the inner layer 44. If by machine, then chucks, for instance, may hold the opposing ends of the mandrel-tubular inner layer 44 assembly while the spiral coil 43 is threaded through an arm on a machine and started onto the tubular inner layer 44 at the initial position as described above. As the chucks rotate, the inner layer 44 rotates, and the arm moves axially down the length of the inner layer 44, thereby applying the coil 43 in a spiral configuration about the inner layer 44. The machine arm moves to a terminating position where the machine or operator cuts the coil before or after hooking the coil 43 onto the inner layer 44.

An operator then applies an outer layer 42 about the coil-inner layer-mandrel assembly. The outer layer 42 may comprise a polyether block amide, nylon, and/or a nylon natural tubing (individually and collectively, "PEBA" and/or "nylon"). The outer layer 42 preferably has a tubular configuration that disposes about (e.g., enveloping, surrounding, wrapping around, covering, overlaying, superposed over, encasing, ensheathing, and the like) a length of the coil-inner layer-mandrel assembly.

Heat shrink tubing, available from many suppliers, including Zeus, Inc. in Orangeburg, S.C. for instance and also Cobalt Polymers in Cloverdale, Calif., may be disposed about the outer layer-coil-inner layer-mandrel assembly. Heating the assembly causes the outer layer 42 to melt. The inner surface of the outer layer 42 thereby seeps through spaces 43' in or between middle layer coils 43 and bonds to both the outer surface of the inner layer 44 and the coils 43. In one embodiment, the inner surface of the outer layer 42 forms a melt bond 47 (explained below) to the outer surface of the inner layer 44. Upon cooling, a solid-state bond results such that the assembly comprises the three layers discussed above. The operator removes the shrink wrap (e.g., by cutting) and withdraws the mandrel. The operator may cut the Flexor® sheath to a desired length for an outer sheath 50 and/or outer guide channel member 80.

The temperature, total rise time, and dwell time for the heat shrink-outer layer-coil-inner layer-mandrel assembly will vary depending on many factors including, for instance, the actual melt bonding material that the outer layer 42 comprises, and also the diameter of the desired Flexor® sheath. For example, the baking parameters for a 2.5 French Flexor® sheath may be approximately 380 degrees Fahrenheit for about five minutes, while the baking parameters for a 4 French Flexor® sheath may be approximately 380 degrees Fahrenheit for about six minutes.

As an alternative to a Flexor® sheath, the outer sheath 50 may comprise a construction of multifilar material. Such multifilar material or tubing may be obtained, for example, from Asahi-Intec USA, Inc. (Newport Beach, Calif.). Materials and methods of manufacturing a suitable multifilar tubing are described in Published United States Patent Application 2004/0116833 (Koto et al.) having an application Ser. No. 10/611,664 and entitled, "Wire-Stranded Hollow Coil Body, A Medical Equipment Made Therefrom and a Method of Making the Same," the contents of which are incorporated herein by reference. Use of multifilar tubing in a vascular catheter device, for instance, is described in U.S. Pat. No. 6,589,227 (Sonderskov Klint, et al.; Assigned to Cook Incorporated of Bloomington, Ind. and William Cook Europe of Bjaeverskov, Denmark), which is also incorporated by reference.

In addition to the outer sheath 50, the middle section delivery device 14 further comprises an inner compression member 41. The delivery device 14 (and, thus, the outer sheath 50 and inner compression member 41) may be constructed to have any diameter and length required to fulfill its intended purposes.

The outer sheath 50, for instance, may be available in a variety of lengths, outer diameters, and inner diameters. In one embodiment, the outer sheath 50 may have a substantially uniform outer diameter in the range from approximately 2 French to approximately 7 French, and in one embodiment the diameter is from approximately 4 French to approximately 5 French in diameter. Otherwise stated, the outer sheath 50 may range from about 0.010 inches to about 0.090 inches in diameter, and in one embodiment the diameter is approximately 0.050 inches. Likewise, the passageway 59 may be available in a variety of diameters. In one embodiment, the inner diameter ranges from about 0.032 inches to about 0.040 inches, and in a preferred embodiment the passageway 59 is approximately 0.032 inches. The diameter may be more or less than these examples, however, depending on the intended vessel passageway for the device. For instance, a larger vessel passageway (e.g., greater expandable inner diameter) may tolerate a bigger device with an outer sheath 50 having a correspondingly greater diameter. Conversely, a narrower vessel passageway may require a thinner outer sheath 50. Likewise, the overall length may vary. In one embodiment, the outer sheath 50 will have a length from about 50.0 cm (or about 19.685 inches) to about 125.0 cm (or about 49.213 inches), and more particularly between about 70.0 cm (or about 27.559 inches) and about 105.0 cm (or about 41.339 inches), and in yet another embodiment the length is approximately 100.0 cm (or about 39.370 inches).

The inner compression member 41 comprises an elongated pusher bar, stiffening member, or stiff polymer that helps to "push" the stent by pushing the stent carrying inner guide channel member at or near the system distal portion 13 in order to counter the urge for the stent or stent carrying member to move as a result of an outer sheath or outer guide channel member being pulled over the stent; thereby "pushing" holds the stent in place at the desired deployment site within the patient's body. The inner compression member 41 "pushes" the stent by helping to prevent or minimize the inner guide channel member from prolapsing, recoiling, kinking, buckling, or moving; thereby keeping the inner guide channel member's stent platform on which the stent is disposed (discussed later) substantially stationary, for the most part, relative to the proximal retraction of the distal outer guide channel member (discussed below) that exposes and, thus, deploys the stent. The phrase "at or near" as used herein to describe an embodiment includes a location that is at, within, or a short distance such as about 0.1 cm to about 15.0 cm, although other ranges may apply, for instance from about 0.5 cm to about 10.0 cm.

The overall length of the inner compression member 41 may vary, as desired. In one embodiment the inner compression member 41 has a length from about 50.0 cm to about 175.0 cm, and more particularly between about 75.0 cm and 150.0 cm, and in one embodiment the length is approximately 125.0 cm to about 140.0 cm. A portion of the inner compression member 41 (e.g., the proximal end 40 and/or middle section 40') may be contained within the handle 30 and the stylet 20, as explained above (FIG. 2).

Likewise, the diameter or width of the inner compression member 41 may vary. In one embodiment, the inner compression member 41 has a diameter or width ranging from about 0.010 inches to about 0.030 inches, by way of example only and not by way of limitation. In one embodiment, the inner compression member 41 has a diameter or width that is approximately 0.016 inches. The diameter or width may be more or less than these illustrative ranges. For example, a deeper target site within a patient may require a thicker inner compression member 41 for greater push-ability, but may tolerate lesser flexibility. In addition, the material that the inner compression member 41 comprises determines whether a smaller and more flexible inner compression member 41 will give suitable flexibility, and also determines whether a wider inner compression member 41 may have the flexibility of a thinner inner compression member 41 made of different material. Furthermore, the inner compression member 41 may have a curved transverse cross-section, such as, for example, a circular cross-section, or it may have a polygonal cross-section, such as, for example, a rectangular cross-section. Alternatively, the transverse cross-section of the inner compression member may include both curved and straight portions. According to one embodiment, the inner compression member 41 may have a nonuniform diameter or width along its length. These various diameters, widths, and cross-sections may occur at the inner compression member proximal end 40, the inner compression member middle section 40', and/or the inner compression member distal mating end portion 48.

It should be understood that the diameter, width, and/or cross-section of the inner compression member 41 may taper. For example, the inner compression member 41 may taper toward the distal end as taught in the U.S. Provisional Patent Application filed on Jan. 23, 2006 entitled, "Tapered Inner Compression Member and Tapered Inner Guide Channel Member for Medical Device Delivery Systems," and having an application Ser. No. 60/761,676, and the non-provisional application filed-on Apr. 20, 2006 by the same title and claiming the benefit of the filing date application Ser. No. 60/761,676 under 35 U.S.C. §119(e), the disclosures of which are incorporated in its entirety.

Also, an inner compression member 41 may have an outer surface comprising a lubricious PTFE material and/or an inner surface 44 of the outer sheath 50 may comprise a lubricious PTFE material against the inner compression member 41, in order to allow easy retraction of the outer sheath 50, which is in communication with a distal outer guide channel member to deploy a self-expanding stent, as will be explained later.

Generally, the inner compression member 41 and outer sheath 50 may optionally be approximately the same in length, and the axial length of coil 43 will be less than the length of the inner compression member and outer sheath. In one embodiment, however, the inner compression member 41 comprises a proximal end 40 that extends proximal relative to the outer sheath. In yet another embodiment, the inner compression member extends to a position that is distal the outer sheath. In still another embodiment, the inner compression member 41 stops short of extending all the way to the distal tip of the delivery system 10, and may stop generally from 10 to 40 cm short of the distal tip of the delivery system 10, and in one embodiment it stops approximately 20 to 25 cm short of the distal tip of the delivery system 10, where the distal end of the inner compression member 41 is lap jointed to a proximal portion of an inner guide channel member (discussed later).

System Distal Portion 13

Now turning to embodiments of a system distal portion 13 of medical device delivery systems, FIGS. 4, 5, 6, and 7 show the system distal portion 13 to be a relatively tubular body. Given the configuration of vessels, vessel passageways, a working channel of an endoscope, or an external accessory channel device used with an endoscepe to be navigated, a mostly tubular distal end with a distal tapered, rounded, chamfered, or arrowhead shape may be better tolerated by the patient. Further, in certain embodiments, the distal portion of the system distal portion 13 may be soft, rounded, and flexible so as to provide further protection for and care to the patient.

Figure 4:
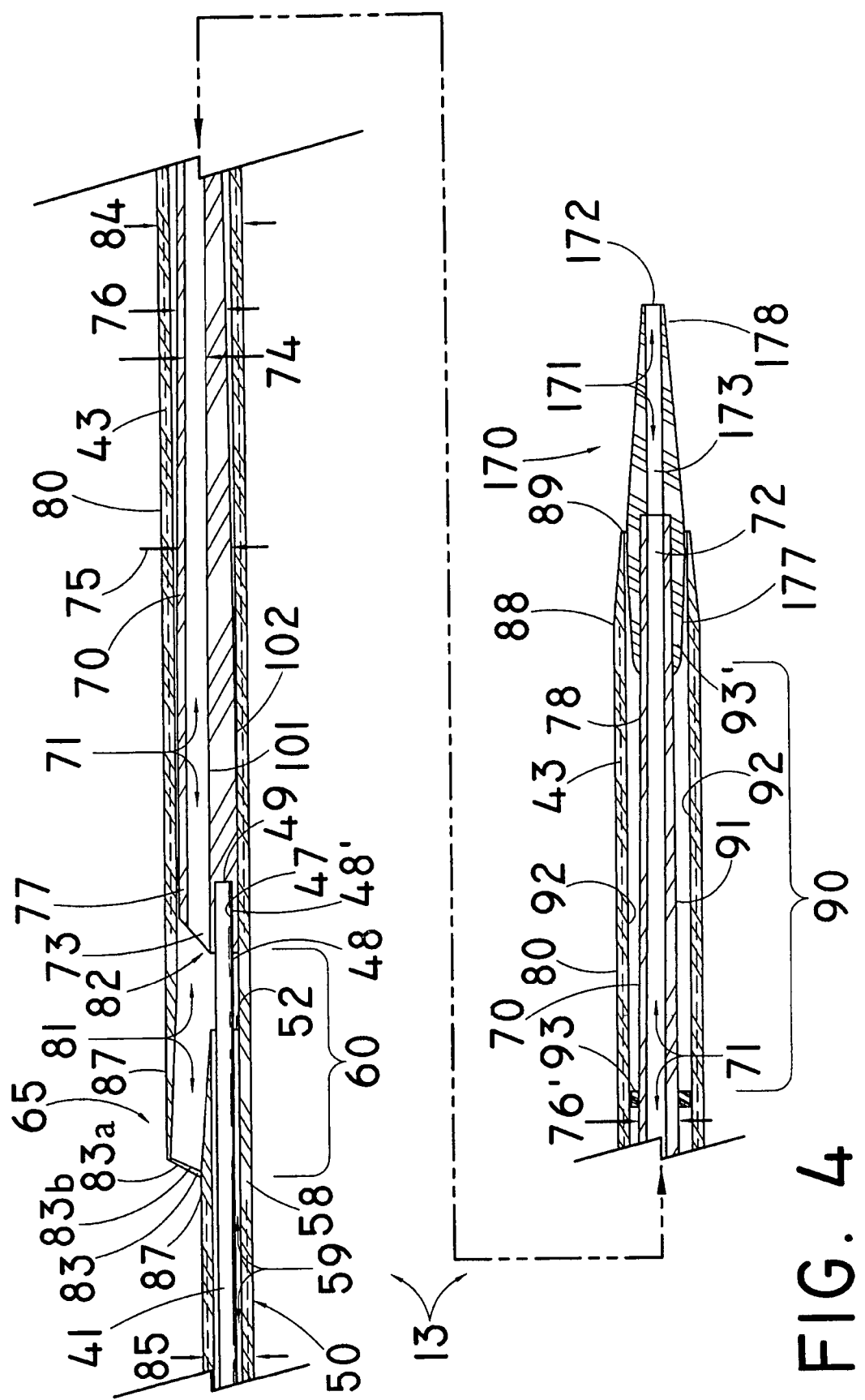
FIG. 4 is a longitudinally sectioned view, broken away, of a system distal portion of medical device delivery system according to one embodiment.
Figure 6:
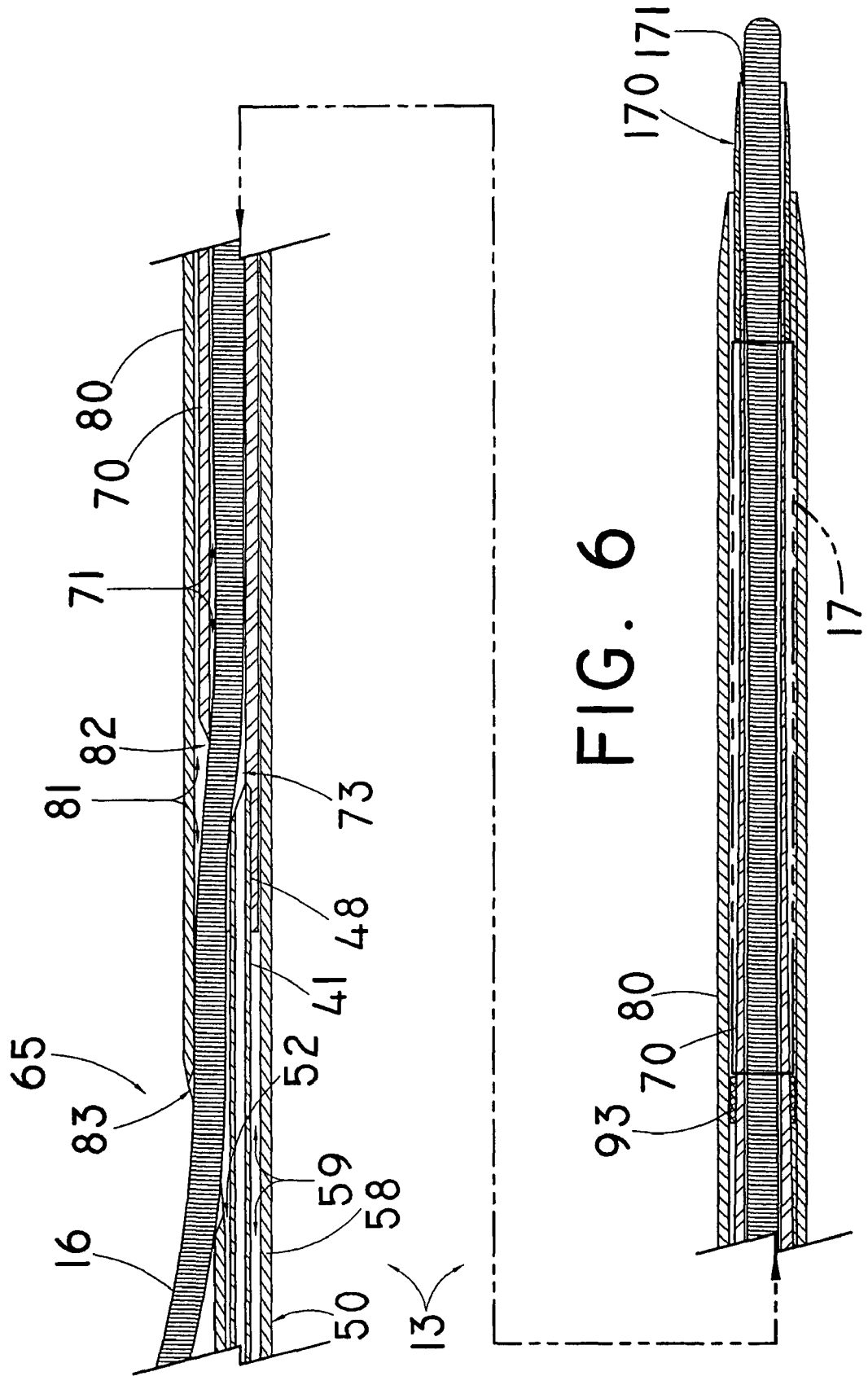
FIG. 6 is a longitudinally sectioned view of an embodiment of a distal portion, shown having a portion of a wire guide.

FIG. 4 illustrates an embodiment of the system distal portion 13 of a delivery system for the rapid insertion of self-expanding stents comprising an inner guide channel member 70, an outer guide channel member 80 axially slideable relative to the inner guide channel member 70, a self-expanding deployment device mounting region 90 (e.g., a stent mounting region), and a transition region 60. As used in connection with describing embodiments of the inner and outer guide channel members 70, 80, respectively, the term "guide channel" is understood to be any passageway, lumen, channel, flow passage, duct, chamber, opening, bore, orifice, aperture, or cavity that facilitates the passage, conveyance, ventilation, flow, movement, blockage, evacuation, or regulation of fluids or gases or the passage of a diagnostic, monitoring, scope, other instrument, and more particularly a catheter, another component of the distal end (e.g., an inner guide channel member 70 relative to the outer member channel 81), or a wire guide 16 (FIG. 6).

The system distal portion 13, according to the delivery system 10 and shown in FIGS. 4, 5, 6, and 7, may be made of any suitable material (natural, synthetic, plastic, rubber, metal, or combination thereof) that is rigid, strong, and resilient, although it should be understood that the material may also be pliable, elastic, and flexible. By way of illustration only and not by way of limitation, the distal end may comprise one or a combination of the following materials: metals and alloys such as nickel-titanium alloy ("nitinol") or medical grade stainless steel, and/or plastic and polymers such as polyether ether-ketone ("PEEK"), polytetrafluoroethylene (PTFE), nylon and/or a polyether block amide ("PEBA"), polyimide, polyurethane, cellulose acetate, cellulose nitrate, silicone, polyethylene terephthalate ("PET"), polyamide, polyester, polyorthoester, polyanhydride, polyether sulfone, polycarbonate, polypropylene, high molecular weight polyethylene, polytetrafluoroethylene, or mixtures or copolymers thereof, polylactic acid, polyglycolic acid or copolymers thereof, polycaprolactone, polyhydroxyalkanoate, polyhydroxy-butyrate valerate, polyhydroxy-butyrate valerate, or another polymer or suitable material. Where it will not contact the patient (e.g., it is contained within a sheath, working channel of an endoscope, or an external accessory channel device used with an endoscope), the middle section delivery device 14 and system distal portion 13 do not need to be biocompatible. In contrast, where there is the possibility of patient contact, the material may need to be biocompatible or capable of being made biocompatible, such as by coating, chemical treatment, or the like.

The inner and outer guide channel members 70, 80, respectively, may be made of any suitable material described above for use with the system distal portion 13. In one embodiment, the inner guide channel member 70 and the outer guide channel member 80 comprise PEEK, which has the advantage of softening under heat before burning or degrading. PEEK tubing may be purchased from many suppliers, such as Zeus, Inc. in Orangeburg, S.C. for instance and also Cobalt Polymers in Cloverdale, Calif.

Beginning with the inner guide channel member 70, a description will follow relating to features common to embodiments of a system distal portion 13 of a delivery system 10 for the rapid insertion of self-expanding stents. The inner guide channel member 70 is generally tubular and comprises a first end portion 78 and a second end portion 77 defining a wire guide channel 71 therebetween. Optionally, the inner guide channel member 70 is configured to be slidably nested, fitted, secured, or otherwise positioned within the outer guide channel member 80 such that at least one of the inner member first or second end portions 78, 77, respectively, is axially intermediate an outer guide channel member first end portion 88 and an outer guide channel member second end portion 87.

The first end portion 78 of the inner guide channel member 70 further comprises a wire guide entry port 72, and the second end portion 77 has a wire guide exit port 73. The entry and exit ports 72, 73, respectively, define and are in communication via the wire guide channel 71. A port, in describing an embodiment of an inner guide channel member 70 and an outer guide channel member 80, includes any structure that functions as a portal, port, passage, passageway, opening, hole, cutout, orifice, or aperture. Thus, the inner guide channel member entry port 72 is sized to receive a wire guide into the inner member guide channel 71, and the inner guide channel member 70 is configured so that the wire guide may exit proximally out the inner guide channel member exit port 73. Optionally, the exit port 73 is located at or near the transition region 60. In one embodiment, the inner guide channel member 70 is a cannula (or catheter) having an entry port 72 and an exit port 73 as previously described and defining a guide channel 71 therebetween.

The inner guide channel member 70 further comprises an outer self-expanding deployment device mounting region 90 (e.g., an outer stent mounting region) positioned intermediate the inner guide channel member entry and exit ports 72, 73, respectively. The length of the inner guide channel member 70 of any of the embodiments may vary generally from about 10.0 to about 40.0 cm. In one alternative embodiment, the length of the inner guide channel member 70 is approximately 15.0 to approximately 25.0 cm. In another embodiment, the length of the inner guide channel member 70 is approximately 20.0 cm. Also, the length of the inner guide channel member 70 may depend on the intended stent, and in another embodiment the length of the inner guide channel member 70 is approximately 15.0 cm for an 8.0 cm stent.

The inner guide channel member 70 further comprises inner and outer diameters. In one embodiment, both diameters are substantially uniform over the entire length of the inner guide channel member 70. By way of example, an internal diameter 74 might measure approximately 0.0205 inches at or near the inner guide channel member proximal second end portion 77, at or near the inner guide channel member distal first end portion 78, and intermediate the first and second end portions 78, 77, respectively. Likewise, an inner guide channel member 70 might have an outer diameter 75 that measures approximately 0.0430 inches. Thus, the outer diameter 75 might measure approximately 0.0430 inches at or near the inner guide channel member proximal second end portion 77, at or near the inner guide channel member distal first end portion 78, and intermediate the first and second end portions 78, 77, respectively.

In an alternative embodiment to an inner guide channel member 70 having a substantially uniform outer diameter 75 along its length from about the second end portion 77 to about the first end portion 78, the inner guide channel member may also comprise a tapered outer diameter 76. In one embodiment, the inner guide channel member tapers distally to a second outer diameter 76' at or near the inner guide channel member first end portion 78 or intermediate the inner guide channel member first and second end portions 78, 77, respectively. The taper 76 has a decreased cross section, diameter, width, height, area, volume, thickness, and/or other configuration, shape, form, profile, structure, external outline, and/or contour relative to the outer diameter 75. In other words, the inner guide channel member second outer diameter 76' is smaller in cross section, diameter, width, height, area, volume, thickness, and/or other configuration, shape, form, profile, structure, external outline, and/or contour than the outer diameter 75.

FIG. 4 further shows an optional atraumatic tip 170 coupled to the inner guide channel member first end portion 78. Extending distally from the inner guide channel member first end portion 78, the atraumatic tip 170 is tapered, rounded, chamfered, or arrowhead shape to be better tolerated by the patient. The atraumatic tip 170 comprises a distal first end portion 178 with a wire guide entry port 172 and a proximal second end portion 177 with a wire guide exit port 173, whereby the entry and exit ports define an atraumatic tip guide channel 171. The ports 172, 173 and channel 171 are sized to slideably receive a wire guide.

The atraumatic tip second end portion 177, as shown in FIG. 4, may abut the outer guide channel member first end portion 88 and, thereby, extend entirely distally beyond a distal opening 89 of the outer guide channel member first end portion 88. Optionally, the outer guide channel member distal opening 89 is spaced from the atraumatic tip 170 sufficient to allow delivery system to be flushed with saline that exits the distal end to remove air in order to help keep air out of the patient, as explained above. In the alternative and as shown in FIG. 5, the atraumatic tip 170 may be configured to have a second end portion 177 that is beveled such that the atraumatic tip second end portion 177 is partially positioned within the outer member guide channel 81 and partially proximal to the outer guide channel member distal opening 89. The beveled design of the atraumatic tip second end portion 177 forms a proximal stop against the outer guide channel member distal opening 89 while permitting the atraumatic tip second end portion 177 to be partially slidably nested, fitted, secured, or otherwise positioned within the outer guide channel member first end portion 88 so that the outer guide channel member first end portion 88 overlaps the atraumatic tip 170 to form a suitable seal that substantially occludes passage of a wire guide between the atraumatic tip 170 and the distal opening 89 of the outer member first end portion 88 (FIG. 5). Furthermore, the atraumatic tip second end portion 177 comprises a stent distal restraint 93' as explained below.

In FIG. 4, the outer guide channel member 80 also is generally tubular and comprises a first end portion 88 and a second end portion 87. The outer guide channel member 80 further comprises a wire guide entry port 82 proximal to the first end portion 88 and a proximal wire guide exit port 83 located at or near the second end portion 87. The entry and exit ports, 82, 83, respectively, define a guide channel 81 of the outer guide channel member 80, wherein the ports 82, 83 and channel 81 are sized to slideably receive a wire guide. The entry port 82 is configured to receive a wire guide into the outer member guide channel 81, and in one embodiment, the entry port 82 is defined by the inner guide channel member exit port 73. In that embodiment, the wire guide moves proximally through the inner member guide channel 71 and egresses from the inner guide channel member exit port 73, wherein the proximal passage of the inner guide channel member exit port 73 is designated as the outer guide channel member wire guide entry port 82. The outer guide channel member proximal wire guide exit port 83 is configured so that a wire guide may egress proximally out the outer member exit port 83. In one embodiment, the outer guide channel member distal opening 89 and exit port 83 define the guide channel 81 therebetween.

In one embodiment, the Flexor® sheath, manufactured and sold by Cook Incorporated of Bloomington, Ind., may be adapted for use with the system distal portion 13 and/or the middle section delivery device 14. Otherwise stated, the Flexor® sheath, as shown in FIG. 3 and described above, may be provided for the system distal portion 13 and/or the middle section delivery device 14. For instance, the system distal portion 13 may be constructed as comprising an integral Flexor® sheath tube with the middle section delivery device 14. Alternatively, a Flexor® tubing may be used for either the middle section delivery device 14 or the system distal portion 13, or both. Then, the separable middle section delivery device 14 and system distal portion 13 may be attached, adjoined, joined, or combined as taught in the U.S. Provisional Patent Application filed on Apr. 20, 2005 entitled, "Delivery System and Devices for the Rapid Insertion of Self-Expanding Devices" and having an application Ser. No. 60/673,199, and the non-provisional application filed on Apr. 20, 2006 by the same title and claiming the benefit of the filing date application Ser. No. 60/673,199 under 35 U.S.C. §119 (e), the disclosures of which are incorporated in its entirety, and/or the U.S. Provisional Patent Application filed on Jan. 23, 2006 entitled, "Melt-Bonded Joint for Joining Sheaths Used in Medical Devices, and Methods of Forming the Melt-Bonded Joint" and having an application Ser. No. 60/761,594, and the non-provisional application filed on Apr. 20, 2006 by the same title and claiming the benefit of the filing date application Ser. No. 60/761,594 under 35 U.S.C. §119 (e), the disclosures of which are incorporated in its entirety.

The Flexor® sheath has a PTFE inner lining 44 that provides a slick, smooth surface for sliding the outer sheath 50 and/or the outer guide channel member 80 proximally. With regard to the system distal portion 13, the outer guide channel member 80 slides relative to the inner guide channel member 70, and the outer guide channel member inner surface 92 would be the inner layer 44 described above, thereby resulting in minimal friction to a stent 17 on the stent platform 91. The slidable inner surface 92 of the Flexor® sheath exhibits a second benefit of minimizing damage or misalignment to the stent. Indeed, because self-expanding stents continuously exert an expanding force against the inside surface 92 of the outer guide channel member 80, any substantial friction or drag between the stent and the inner surface 92 of the outer guide channel member 80 as the outer guide channel member 80 withdraws may damage the stent or cause the stent to be deployed slightly off of the target site.

The thin flat wire reinforcing coil 43 of the Flexor® sheath provides the outer guide channel member 80 with the necessary radial strength to constrain the stent over long periods of storage time. In contrast, where the inner surface 92 of an outer guide channel member 80 does not comprise the Flexor® sheath inner layer 44 or equivalent, the stent over time may tend to become imbedded in the inner surface 92 and, as a result, interfere with retraction of the outer guide channel member 80 at the time of deployment. In an outer guide channel member 80 that comprises a Flexor® sheath, in addition to the inner layer 44 and the reinforcing coil 43, the outer guide channel member 80 has a Flexor® sheath outer layer 42. The outer layer 42 comprises nylon and/or PEBA to provide the necessary stiffness for pushability, retraction, and control of the outer guide channel member 80 to facilitate proper deployment of the constrained self-expanding stent. Therefore, the Flexor® sheath is one non-limiting example of an embodiment of an outer sheath 50 and/or an outer guide channel member 80.

While FIG. 4 shows an outer guide channel member 80 having the exit port 83 proximal to the entry port 82 in one embodiment of the outer guide channel member 80, the relative axial distances between the entry and exit ports 82, 83, respectively, vary when the outer guide channel member 80 is in a non-deployed state versus a deployed state, because the outer guide channel member 80 moves axially relative to the inner guide channel member 70. Otherwise stated, FIG. 4 shows an embodiment where the exit port 83 is proximal to the entry port 82 in either a non-deployed stent position or in a deployed stent position. In a non-deployed stent position of another embodiment, however, the exit port 83 may be substantially co-planar to or aligned with the entry port 82. In the fully deployed stent position, the exit port 83 may likewise be proximal, co-planar, or aligned with the entry port 82. Optionally, the entry port 82 and exit port 83 are located at or near the transition region 60 to be discussed below.

Furthermore, the outer guide channel member 80 has a stepped 84, 85 profile, whereby the outer guide channel member 80 comprises a first outer diameter 84 intermediate the outer guide channel member first and second end portions 88, 87, respectively, and a second smaller outer diameter 85 located at or near the outer guide channel member second end portion 87 in the vicinity of the transition region 60 and the breech position opening 65. The stepped 84, 85 profile includes an embodiment where the outer guide channel member 80 transitions to the distal end portion 58 of the outer sheath 50 of the middle section delivery device 14. In describing embodiments, however, the stepped 84, 85 profile shall be discussed in reference to the outer guide channel member 80 in particular, but it should be understood as including a stepped 84, 85 profile in reference to the transition region 60 of the system distal portion 13 relative to the middle section delivery device 14 where the middle section delivery device 14 and system distal portion 13 are formed from separate units such as, by way of example only and not by way of limitation, separate "Flexor®" sheaths where one comprises a first outer diameter 84 and the other comprises a second smaller outer diameter 85.

As shown in FIG. 4, the second smaller outer diameter 85 of the outer guide channel member 80 is located proximal to the larger first outer diameter 84 and, thereby, comprises a stepped 84, 85 profile. Having a second smaller outer diameter 85 reduces the profile of the outer guide channel member 80 and/or the outer guide channel member 80 transition to the middle section delivery device 14, which is advantageous in procedures involving narrow vessel passageways, endoscope working channels, or accessory channels for use with endoscopes. The difference in the first diameter 84 and the second diameter 85 may vary. By way of illustration, the second diameter 85 may be approximately one-fourth to approximately nine-tenths that of the first diameter 84. In another embodiment, the second diameter 85 may be about one-half that of the first diameter 84. In another embodiment, the first diameter 84 is roughly 5 French while the second diameter 85 is roughly 4 French.

In one embodiment of the stepped 84, 85 profile of the outer guide channel member 80, the second smaller outer diameter 85 is located at or near the outer guide channel member second And portion 87. The second end portion 87 may decrease precipitously from the first outer diameter 84 to the second smaller diameter 85. In a precipitous step, the change from the diameters occurs over a short length along the longitudinal axis of the system distal portion 13. In a further example of a precipitous step, the plane formed by the exit port 83 may be substantially perpendicular to the longitudinal axis of the outer guide channel member 80. In an alternative embodiment, the second end portion 87 may decrease gradually from the first outer diameter 84 to the second smaller diameter 85. In a gradual step, the change from the two diameters occurs over a length of more than 1.0 millimeter ("mm") along the longitudinal axis of the system distal portion 13 at or near the transition region 60 and breech position opening 65, and in one instance this change occurs over a length from about 1.0 mm to about 10.0 mm. In a further example of a gradual step, the plane formed by the exit port 83 may be at an angle other than 90 degrees relative to the longitudinal axis of the system distal portion 13.

FIG. 4 also shows a breech position opening 65 located at or near the second end portion 87 of the outer guide channel member 80 comprising the wire guide exit port 83. In other words, rather than the exit port 83 being an aperture in a sidewall of the outer guide channel member 80 intermediate the first and second end portions 88, 87, respectively, in a breech position opening 65 embodiment the exit port 83 is at the rear, back, or proximal part of the system distal portion 13 at or near the outer member second end portion 87 and the stepped 84, 85 profile such that it opens in the direction of the outer surface of the outer sheath 50.

The breech position opening 65 may be used for front-loading and the more common procedure of back-loading a wire guide (or catheter, for instance). In a back-loading procedure for a delivery system having a breech position opening 65, the wire guide may pass proximally through the guide channel 71 of the inner guide channel member 70, proximally through the guide channel 81 of the outer guide channel member 80, and leave the exit port 83 of the second end portion 87 of the outer guide channel member 80 from a breech position opening 65 in a rear, back, or proximal part of the system distal portion 13. Conversely, in a front-loading procedure for a delivery system having a breech position opening 65, the physician may feed the wire guide distally into a breech position opening 65 at the rear, back, or proximal part of the system distal portion 13 by entering the exit port 83 of the second end portion 87 and the guide channel 81 of the outer guide channel member 80 and through the guide channel 71 of the inner guide channel member 70, where the wire guide may exit from the wire guide entry port 72 of the inner guide channel member 70 and/or wire guide entry port 172 of the atraumatic tip 170.

In a system distal portion 13 having a breech position opening 65 that comprises an exit port 83 located at a breech position of the transition region 60, the wire guide does not need to make any sharp turns away from the longitudinal axis of the system distal portion 13 that may result in kinking of the wire guide. The breech position opening 65—comprising an exit port 83, as shown in FIGS. 4, 5, 6, and 7 by way of example and not by way of limitation—is located proximal to the inner guide channel member second end portion 77 and may be transverse or angled relative to the tubular system distal portion 13 longitudinal axis. In other words, the wire guide exit port 83 may be positioned at or near a breech position opening 65 of the system distal portion 13, wherein the exit port 83 is located at or near the rear, back, or proximal part of the outer guide channel member 80 and/or second end portion 87, rather than being positioned exclusively on the side (e.g., outer circumference) of the outer guide channel member's 80.

In FIG. 4, the breech position opening 65 comprises an exit port 83 that is illustrated as being oblique, although other configurations of the exit port may be utilized to aid the wire guide in exiting the rear of the outer member. In one example, the exit port 83 may form a plane substantially perpendicular to the longitudinal axis of the outer guide channel member second end portion 87. In another example, the plane formed by the exit port 83 may be at an angle other than 90 degrees relative to the longitudinal axis of the system distal portion 13. Optionally, the oblique exit port 83 of a breech position opening 65 has lateral walls 83a, 83b that act as guide rails to direct a wire guide proximally toward the middle section delivery device 14 and to run along the outside of the outer sheath 50.

The overall axial length of the exit port 83 of the breech position opening 65 may vary. In one embodiment, the length is approximately from about 1.0 mm to about 10.0 mm. Another embodiment has a length of approximately 5.0 mm. The overall width of the exit port 83 may also vary. In one example, the width of the exit port is approximately 1 French. In yet another instance, the width of the exit port 83 ranges from about 1 French to about 4 French. In another example, the width of the exit port 83 may be the approximate difference between the first outer diameter 84 and the second outer diameter 85 of the outer guide channel member 80.

At the transition region 60, the exit port 73 of the inner guide channel member 70 is in communication with the outer guide channel member 80 wire guide entry port 82, while the second end portion 77 is operatively coupled to the distal mating end portion 48 of the inner guide channel member 70 as explained below. The length of the transition region 60 may vary. For instance, the transition region 60 may be approximately from about 0.5 cm to about 10.0 cm. In another embodiment, the transition region 60 has the approximate length of about 5.0 cm. Furthermore, the length of the transition region 60 is variable: from a shorter axial length when the outer guide channel member 80 is in a non-deployed axial position; to a greater axial length when the outer guide channel member 80 retracts proximally to deploy the stent. Likewise, the overall length of the transition region 60 varies in the embodiment where the exit port 83 is distal to the entry port 82 when the outer guide channel member 80 is in a non-deployed stent position, compared to the initial length of the transition region 60 in an embodiment where the exit port 83 is proximal to the entry port 82 when the outer guide channel member 80 is in a non-deployed stent position.

In one use of the transition region 60 according to an embodiment, the outer guide channel member entry port 82 receives a wire guide from the inner guide channel member exit port 73 and the wire guide thereby is received in the outer member guide channel 81. At the transition region 60, the inner member guide channel 71 and outer member guide channel 81 are approximately aligned relatively coaxially in one embodiment. Approximate alignment of the guide channels 71, 81 facilitates a smooth transition of the wire guide. Smooth transition optimally reduces any bending of the wire guide as the wire guide moves proximally from the inner member guide channel 71 to the outer member guide channel 81.

As shown in FIG. 4, the system distal portion 13 also comprises a self-expanding deployment device mounting region 90. This mounting region 90 may be used for implantable prosthesis such as expandable (self-expanding, balloon expandable, or otherwise expanding) and nonexpanding stents, prosthetic valve devices, and other implantable articles for placement inside a patient's body (the implantable prostheses being referred to individually and collectively as "stents" without limiting the invention) and therefore may be referred to as a stent mounting region to include the foregoing implantable prostheses.

The stent mounting region 90 comprises a stent platform 91 on an outside surface of the inner guide channel member 70 located at or near the inner guide channel member second end portion 77. In describing embodiments, the platform 91 "at or near" the inner guide channel member second end portion 77 includes a region intermediate the inner guide channel member entry port 72 and the inner guide channel member exit port 73. The platform 91 may be any stent mounting surface, including but not limited to the outside surface of the inner guide channel member 70, a recess, or an indentation located at or near the first end portion 78 of the inner guide channel member 70. In a non-deployed state, a self-expanding stent for example (not shown) compresses against the stent platform 91 and disposes around the outside of the inner guide channel member 70.

The stent mounting region 90 controls the lateral movement (e.g., transverse expansion away from the inner guide channel member longitudinal axis) to avoid premature deployment of the stent. In order to control the lateral movement of the stent, the stent is sandwiched between the platform 91 on the inner surface of the stent and the inner surface 92 of the outer guide channel member 80 to keep the stent in a compressed state. Because the stent is bound from above by the inner surface 92 of the outer guide channel member 80 and bound from below by the platform 91 of the inner guide channel member 70, the stent mounting region 90 maintains the stent in a substantially compressed state and controls premature deployment of the stent.

In addition to controlling a stent's lateral movement, the stent mounting region 90 restrains the axial movement of a stent to control the stent movement away from the target site. A proximal restraint 93 controls proximal axial movement of the stent. In one embodiment, the proximal restraint 93 is sized to be large enough to make sufficient contact with the loaded proximal end of the stent without making frictional contact with the inner surface 92 of the outer guide channel member 80. In addition to helping to stop the stent's proximal movement in the non-deployed state, this restraint 93 assists with "pushing" the stent out of the system distal portion 13 by helping to prevent the inner guide channel member 70 and/or the stent disposed on the stent mounting region 90 from migrating proximally when the outer guide channel member 80 retracts proximally relative to the stationary inner guide channel member 70 in order to expose and deploy the stent. Optionally, the restraint 93 may be radiopaque so as to aid in stent positioning within the vessel passageway at or near the target site within a patient. In one embodiment, an optional distal restraint 93' is large enough to make sufficient contact with the loaded distal end of the stent to control axially distal movement of the stent. Similarly, in another embodiment the proximal second end portion 177 of an optional atraumatic tip 170 controls the stent's distal axial movement. Indeed, because the medical device delivery system may be used for deploying an implantable prosthesis that comprises balloon expandable or non-expanding stents, prosthetic valve devices, and other implantable articles at a selected location inside a patient's body, the proximal restraint 93 and distal restraint 93' control the axial distal movement of the implantable prosthesis. Optionally, the distal restraint 93' and/or atraumatic tip 170 may comprise radiopaque materials so as to aid in stent positioning within the vessel passageway at or near the target site within a patient.

FIG. 4 also illustrates that the inner compression member 41 and inner guide channel member second end portion 77 may be operatively coupled by any suitable means. In one embodiment, a melt bond 47 (described below) operatively couples an inner compression member distal mating end portion 48 ("mating end portion 48") and the second end portion 77 of the inner guide channel member 70. A melt bond 47 provides surface-to-surface contact between the outer engaging surface 48' of the mating end portion 48 and the inner guide channel second end portion 77, thereby forming a more solid connection between the inner compression member 41 and the inner guide channel member 70.

In one embodiment, the inner compression member outer engaging surface 48' may form a melt bond 47 to an inner surface 101 of the inner guide channel member second end portion 77. Alternatively, the inner compression member outer engaging surface 48' may form a melt bond 47 to the outer surface 102 of the inner guide channel second end portion 77. In yet another embodiment, the distal mating end portion 48 of a solid inner compression member 41 as shown in FIG. 4 is implanted 49 between (and/or melt bonded 47 to one or both of the) inner and outer surfaces 101, 102, respectively, of the inner guide channel member second end portion 77, as taught in U.S. Provisional Patent Application filed on Jan. 23, 2006 entitled, "Internal Joint for Medical Devices, and Methods of Making the Internal Joint," and having an application Ser. No. 60/761,313, and the non-provisional application filed on Apr. 20, 2006 by the same title and claiming the benefit of the filing date application Ser. No. 60/761,313 under 35 U.S.C. §119(e), the disclosures of which are incorporated in its entirety. In still another embodiment, an insert body operatively couples the inner compression member 41 and the second end portion 77 of the inner guide channel member 70, as taught in U.S. Provisional Patent Application filed on Jan. 23, 2006 entitled, "Internal Cannulated Joint for Medical Delivery Systems," and having an application Ser. No. 60/761,565, and the non-provisional application filed on Apr. 20, 2006 by the same title and claiming the benefit of the filing date application Ser. No. 60/761, 565 under 35 U.S.C. §119(e), the disclosures of which are incorporated in its entirety.

As used to describe an embodiment, melt bonding 47 (for shorthand purposes melt bonding 47 includes implanting 49) comprises any suitable means for melting, liquefying, softening, making tacky, fusing, or making malleable, pliant, supple, moldable, ductile, or otherwise penetrable by another component or fused to melt bonding material comprising the other element. For instance, melt bonding 47 involves bringing two components together at an interface, wherein one (or preferably both) of the component interfaces are in the melted state. Strictly speaking, true melt bonding 47 requires that both of the components be melted at the interface and that they may be sufficiently chemically and physically compatible such that they fuse together upon cooling.

The melt bonding materials comprising the two components may be the same or substantially same materials. In the alternative, the melt bonding materials may be different, so long as they have substantially similar melting points at standard atmospheric pressure such that the materials soften (or liquefy) under heat and thereby fuse together in a solid state melt bond 47 joining the first and second melt bonding materials of the components. If the materials had melting points that were too different, then one material may degrade or burn and the like before the second material begins to melt.

Melt bonding 47 may be single layer interface whereby one component interface/surface mates to a second component interface/surface, or may be multi-layer interface whereby one component is implanted 49 into a second component and then surrounded by the second component. The chemical compatibility can best be expressed in terms of having similar values for surface energy and/or solubility parameter. In simple terms, similar materials tend to have a mutual affinity and a greater propensity to adhere to one another than do dissimilar materials. As used here, melt bonding includes bonding whereby one component is melted while the other component is at or above its melting point.

In general, melt bonding materials have different "melt bonding" temperatures at which the material will soften and become almost tacky without substantial degradation. Melt bonding materials are available from vendors, including Zeus, Inc. in Orangeburg, S.C. for instance and also Cobalt Polymers in Cloverdale, Calif. The melt bonding materials may include one or a combination of a class of suitable materials comprising nylon, nylon natural tubing, polyether block amide, polyetheretherketone, thermoplastic, acrylonitrile-butadiene-styrene copolymer, polypropylene, polyamide, ionomer, polycarbonate, polyphenylene oxide, polyphenylene sulphide, acrylic, liquid crystal polymer, polyolefin, polyethylene acrylate acid, polyvinylidene fluoride, polyvinyl, and polyvinyl chloride.

In one embodiment, PEEK material is used for the melt bonding material. PEEK melts at about 633° F., so the material may be heated from about 628° F. to about 638° F. For instance, a radiofrequency loop heater may be used for heating the melt bonding materials. Such a machine is available from Magnaforce, Incorporated and sold under the name and model Heatstation 1500. Another such machine is available from Cath-Tip, Inc. and is sold under the model and name Cath-Tipe II. There is a rise dwell and cool down time for the process. The total rise time is approximately 20 seconds and dwell time is approximately 10 seconds. During the dwell time the temperature is approximately 600° F. In one embodiment where nylon or PEBA are used, heating is at about 400° F., with dwell time of about 10 seconds.

FIGS. 4A and 4B present a schematic representation of a cross section 105 of components before and after melt bonding according to one embodiment. The cross section 105 of FIG. 4A, for example, represents an inner component 106, middle component 107, and outer component 108. While all components are shown having abutting interfaces in physical abutting contact, they need only be close enough to form a melt bond therebetween. Indeed, as previously explained in connection with the Flexor® sheath's outer layer 42 and inner layer 44, there may even be a middle layer comprising a coil 43 having spacings 43' through which the melt bonding material of the outer layer 42 may move to be into contact with the inner layer 44.

In the example represented in FIG. 4A, the middle and outer components 107, 108, respectively, are intended to be melt bonded. The middle component 107 comprises a first melt bonding material 109 while the outer component 108 comprises a second melt bonding material 109', which may be the same material or may be separate materials that have similar melting points at atmospheric pressure.

FIG. 4B shows some of the first melt bonding material 109 of the middle component 107 moving into some of the second melt bonding material 109' of the outer component 108. Likewise, some of the second melt bonding material 109' of the outer component 108 moves into some of the first melt bonding material 109 of the middle component 107. It should be noted that both of the first and second materials 109, 109' need not move into the other. Rather, the first and second materials 109, 109' need only bond at an interface, with or without mixing and the like. By way of example, the Flexor® sheath's outer layer 42 may melt to the middle layer coil 43 (which has not melted) and bond to the outer surface of the inner layer 44 with or without the outer surface of the inner layer 44 melting into the outer layer 42.

FIG. 4B further shows that the first and second melt bonding materials 109, 109', for the middle component 107 and the outer component 108 or other components that have been melt bonded, are cooled to solid state to form a melt bond 47 operatively coupling the components and/or the melt bonding materials that comprise the components. This results in additional strength and helps to form a more solid connection to the melt bonded components, because a solid-state bond results from using a suitable form of heat for melting and solidifying (e.g., fusing and/or cross-linking bonds formed at the melt bonded material interfaces).

FIG. 5 illustrates a schematic view showing an alternative embodiment of a system distal portion 13 of a delivery system for the rapid insertion of stents comprising an inner guide channel member 70, an outer guide channel member 80 axially slideable relative to the inner guide channel member 70, a deployment device mounting region 90 (e.g., a stent mounting region), and a transition region 60. Like elements from the previous drawings, embodiments, and description from above are labeled the same. In this embodiment, the inner compression member 41 optionally comprises a passageway 45 (e.g., hollow, having a lumen) that facilitates the conveyance, ventilation, flow, movement, blockage, evacuation, or regulation of medication and/or fluids or accommodates the insertion of a diagnostic, monitoring, scope, or other instrument.

The tubular inner compression member 41 may have a uniform inside diameter ranging from about 0.0527 to about 0.132 inches. The wall thickness of the tubular inner compression member 41 is approximately 0.0015 inch. These dimensions are illustrative only, and the inner diameter and wall thickness may be constructed to be of any size necessary to accomplish the purposes for which the delivery system is to be employed (i.e., limited by the vessel passageway or working channel in which the device is to be used).

In addition, this inner compression member 41 has an optional distal one-way valve 61. Thus, the valve 61 may serve a dual function. First, a one-way valve is relatively resistant to contamination from bodily fluids entering the inner compression member passageway 45. Second, it allows the movement of medication and/or fluids to exit distally the inner compression member 41 passageway 45 at or near the transition region 60 and may direct medication and/or fluids into the inner member guide channel 71 and/or the outer member guide channel 81.

Indeed, the inner compression member passageway 45 may facilitate using the medical device delivery system for deploying an implantable prosthesis that comprise balloon expandable stents, prosthetic valve devices, and other implantable articles (individually and collectively, "stent") at a selected location inside a patient's body. The stent is disposed at the deployment device mounting region 90 intermediate the proximal restraint 93 and distal restraint 93' to control the axial distal movement of the implantable prosthesis.

In one embodiment for using the delivery system with a balloon expandable implantable prosthesis, the inner compression member distal mating end portion engaging surface 48' operatively couples to the inner guide channel member outer surface 102 (or is welded to an outer surface of a metal cannula that has the inner guide channel member second end portion 77 glued within the cannula lumen), and an inflation member (e.g., a balloon) extends distally from the inner compression member mating end portion 48 and is disposed over the proximal restraint 93 and distally about the platform 91 of the stent mounting region 90 such that the balloon is located under the stent. The stent is positioned within the vessel passageway at or near the target site within a patient, wherein the outer sheath 50 and outer guide channel member 80 is axially slideable relative to the inner compression member 41 and inner guide channel member 70 upon corresponding axial slideable movement of the handle 30, thereby exposing and, ultimately, deploying the stent from Ache stent mounting region 90. The stylet 20 may be adapted to receive a syringe for allowing inflation fluid, such as saline, to travel from and through the proximal end 40 of the inner compression member 41 and out the valve 61 at the distal mating end portion 48 in order to fill the inflation chamber of the balloon. Therefore, balloon expands under the stent and, as a result, the stent expands radially to plastically deform the stent into a substantially permanent expanded condition. The physician then deflates the balloon and removes the inner guide channel member 70 and remainder of the delivery system from the patient's body. This description of using the delivery system for balloon expandable implantable prosthesis is given by way of example and not by way of limitation.

In one embodiment of the system distal portion 13 of a delivery system illustrated in FIG. 5, an internal joint 46 comprises a melt bond 47 that operatively couples an inner guide channel member mating end portion 48 ("mating end portion 48") and the second end portion 77 of the inner guide channel member 70. For example, the inner compression member outer engaging surface 48' may form a melt bond 47 to an inner surface 101 of the inner guide channel member second end portion 77, as taught above. Alternatively, the inner compression member outer engaging surface 48' may form a melt bond 47 to the outer surface 102 of the inner guide channel second end portion 77, as taught above.

The embodiment shown in FIG. 5 also illustrates that the exit ports 83 and 73 may have various configurations. First, these exit ports curve, and second, compared to FIG. 4 they slope over a longer overall axial length to aid the wire guide in exiting the inner member and outer member, respectively. Furthermore, the exit port 83 thereby has longer axial lateral walls 83*a*, 83*b* for acting as guide rails to direct a wire guide proximally toward the middle section delivery device 14 and to run along the outside of the outer sheath 50.

Moving to the atraumatic tip 170 as illustrated in FIG. 5, this is a little less arrowhead-shaped compared to the atraumatic tip 170 shown in FIG. 4. Instead, the atraumatic tip in FIG. 5 has a second end portion 177 that comprises a right cylindrical tubular configuration. Furthermore, the sides of the atraumatic tip second end portion 177 are more uniformly parallel and do not form a proximal stop against the outer guide channel member distal opening 89 as in a beveled embodiment of the atraumatic tip second end portion 177 as illustrated in FIG. 4. The atraumatic tip second end portion 177 optionally comprises a stent distal restraint 93' for controlling distal axial movement of the implantable prosthesis when the medical device delivery system is used for deploying balloon expandable or non-expanding stents, prosthetic valve devices, and other implantable articles at a selected location inside a patient's body.

Turning now to FIG. 6, that figure shows a partially sectioned system distal portion 13 in accordance with an embodiment of the device according to FIG. 5 with a wire guide 16 inserted therein. In a back-loading procedure, the wire guide 16 enters the guide channel 171 of the atraumatic tip 170 and travels proximally toward the inner guide channel member 70. The wire guide 16 then enters the inner member guide channel 71 and travels proximally toward the outer guide channel member 80 via the entry port 82 and enters the outer member guide channel 81 and out the exit port 83. The less common front-loading procedure could be described as above but conversely stated.

In FIG. 6, the inner and outer guide channels 71, 81, respectively, are substantially aligned coaxially along an approximate center longitudinal axis of the system distal portion 13. Because the channels 71, 81 are substantially aligned, the wire guide 16 moves through the inner member guide channel 71 to the outer member guide channel 81 and out the outer guide channel member exit port 83 at or near the breech position opening 65 with relatively little kinking, bending, buckling, or bowing. It should be noted that for the ease of showing the wire guide 16, the wire guide 16 proximal to the exit port 83 is shown slightly offset from outer sheath 50, though the wire guide 16 may actually run along the outside of the outer sheath 50 or in a groove (not shown) in the outer sheath 50.

FIG. 7 illustrates a longitudinally sectioned side view showing an alternative embodiment of a distal portion 13 of a delivery system for the rapid insertion of stents comprising an inner guide channel member 70, an outer guide channel member 80 axially slideable relative to the inner member 70, a deployment device mounting region 90 (e.g., a stent mounting region), and a transition region 60. Like elements from the previous drawings, embodiments, and description from above are labeled the same. This embodiment represents an alternative embodiment of a joint 46 for operatively coupling the inner compression member 41 and inner guide channel member 70 with a cannula 95.

In one embodiment, the cannula 95 is a hollow, rigid tube, cylinder, ring, cannula (with or without a trocar), or other coupling device comprising metal such as medical grade stainless steel or super-elastic alloys (e.g., nitinol) to name but a few non-limiting examples. In one embodiment, the cannula 95 comprises a generally right cylindrical configuration or is elliptical, hyperbolic, parabolic, curved, polygonal, rectangular, or irregular in shape or cross section. The cannula 95 is sized for receiving the inner guide channel second end portion 77 and/or the inner guide channel second end portion outer diameter 75. The outer surface 102 of the inner guide channel second end portion 77 is operatively coupled to an inner engaging surface of the securing body 95 by glue, adhesives, resins, chemical bonding materials or combinations thereof and the like (collectively and individually, "glue"). By way of example only, the glue may be Loctite 4061 instant adhesive, formulated to polymerise rapidly in thin films between two surfaces to form rigid thermoplastics. Loctite 4061 instant adhesive is a medical device adhesive particularly suitable for a wide variety of substrates such as rubber, plastics, and metals, ant it is available from the Loctite Corporation.

In addition to securing the outer surface 102 of the inner guide channel member second end portion 77 to an inner engaging surface of the cannula 95, the cannula 95 also operatively couples the inner guide channel member distal mating end portion 48. An outer engaging surface 48' of the mating end portion 48 is in an abutting relationship (e.g., touching, in contact directly or by intervening parts, or adjacent) to an outer engaging surface of the cannula 95, and the distal mating end portion 48 and cannula 95 are operatively coupled by any suitable means, including but not limiting to welding, soldering, brazing, or fusing. Soldering and brazing are used if a semi-permanent connection between the distal mating end portion 48 and the cannula 95 is desired, because solder or braze metals have a lower melting point than the metals that are joined. Thus, when sufficient heat is applied to melt the solder or braze metal, they form an alloy with the surfaces of the distal mating end portion 48 and the cannula 95 and, upon solidification, thus form a joint that can be unfastened during manufacturing (e.g., to redo in the event of a poor connection) by reheating without destroying the parts that have been joined. In contrast, welding involves melting the outer engaging surface 48' of the distal mating end portion 48 and an outer engaging surface of the cannula 95 at the interface, or involves combining temperature and pressure so as to cause localized coalescence. Consequently, in most instances higher temperatures are involved than for soldering, and the union is permanent.

Where the inner compression member distal mating end portion 48 and the cannula 95 are connected, an optional tube may be disposed about the joint 46. The tubing has the advantage of minimizing some of the sharp edges created by a welded, soldered, or fused joint. In one embodiment, the tube is a melt bonding tube disposed about and melt bonded to the joint 46. Whereas FIG. 7 shows the distal most tip of the distal mating end portion 48 flush with (e.g., substantially co-planar) the distal end portion of the cannula 95, it may alternatively be set back approximately 0.5 mm proximally from the distal end portion of the cannula 95. The set back arrangement allows solder, weld, or fusion to form a smooth transition and fill the space between that distal end tip and the cannula 95. This would also minimize the profile compared to placing more of a circumferential solder, weld, or fusion about the joint.

According to FIGS. 7, 7A, 7B, and 7C, the distal mating end portion 48 comprises a contoured configuration 48" that is complementary to an outer engaging surface 95' of the cannula 95. Thus, in an embodiment comprising a cannula 95 that is curved or otherwise circular in cross-section, then FIG. 7A shows that the contoured configuration 48" is fluted so that the outer engaging surface 48' is capable of being in an abutting relationship (e.g., touching, in contact directly or by intervening parts, or adjacent) relative to a curved or circular outer engaging surface 95' of the cannula 95. A fluted contoured configuration 48" comprises any curved, shoehorn shape, celery shape, semicircular shape, crescent shape, wishbone shape, saddle shape, C-shaped, V-shaped, U-shaped, or other arcuate configuration. In another embodiment, an outer engaging surface 95' of the cannula 95 could have a flat portion, and FIG. 7B shows that the contoured configuration 48" is likewise flat so that the outer engaging surface 48' is capable of being in an abutting relationship (e.g., touching, in contact directly or by intervening parts, or adjacent) relative to the flat portion of the outer engaging surface of the cannula 95. Even when the outer engaging surface 95' of the cannula 95 is curved or circular in cross section, however, FIG. 7C shows that the inner compression member contoured configuration 48" could be flat, because the soldering, brazing, or fusing may fill in the space between the outer engaging surface 48' and a tangent that the flat configuration 48" forms to the curved portion of the outer surface 95' of the cannula 95. Similarly, if welding 96 is used, then the flat configuration 48" will form to a curved or circular outer engaging surface 95' of the cannula 95.

In addition, the contoured configuration 48" maintains low profile, high-strength, and flexibility of the connection between the inner compression member distal mating end portion 48 and the cannula 95. The contoured configuration 48" is in contrast to a rounded inner compression member distal mating end portion 48, which would have a greater diameter at the connection between the inner compression member distal mating end portion 48 and the cannula 95.

In order to create the contoured configuration 48", the inner compression member distal mating end portion 48 may be formed, sheared, casted, or molded. By way of example only, forming can be done both hot and cold (except for stamping, which is always done cold) in order to modify the shape and/or physical properties of the material comprising the inner compression member distal mating end portion 48. Common forming processes include rolling the distal mating end portion 48 (between one or two rollers), stretching, forging, straight bending, and stamping.

Additional embodiments of the joint 46, cannula 95, and inner compression member distal mating end portion 48 comprising a contoured configuration 48" are described in the U.S. patent application filed on Apr. 20, 2006 entitled, "Joint for Operatively Coupling a Contoured Inner Compression Member and an Inner Guide Channel Member for Medical Device Delivery Systems" and having a client reference number PA-5930-RFB, the disclosure of which is incorporated in its entirety.

Flared Strain Relief Member

Described herein is a strain relief member operatively coupled to an outer sheath and used for a medical device delivery system for deploying an implantable prosthesis (e.g., a self-expanding, balloon expandable, or non-expanding stent; prosthetic valve devices, and other implantable articles) at a selected location inside a patient's body. The device may further comprise a handle that operatively couples the strain relief member for use in said medical device delivery system.

Figure 9:
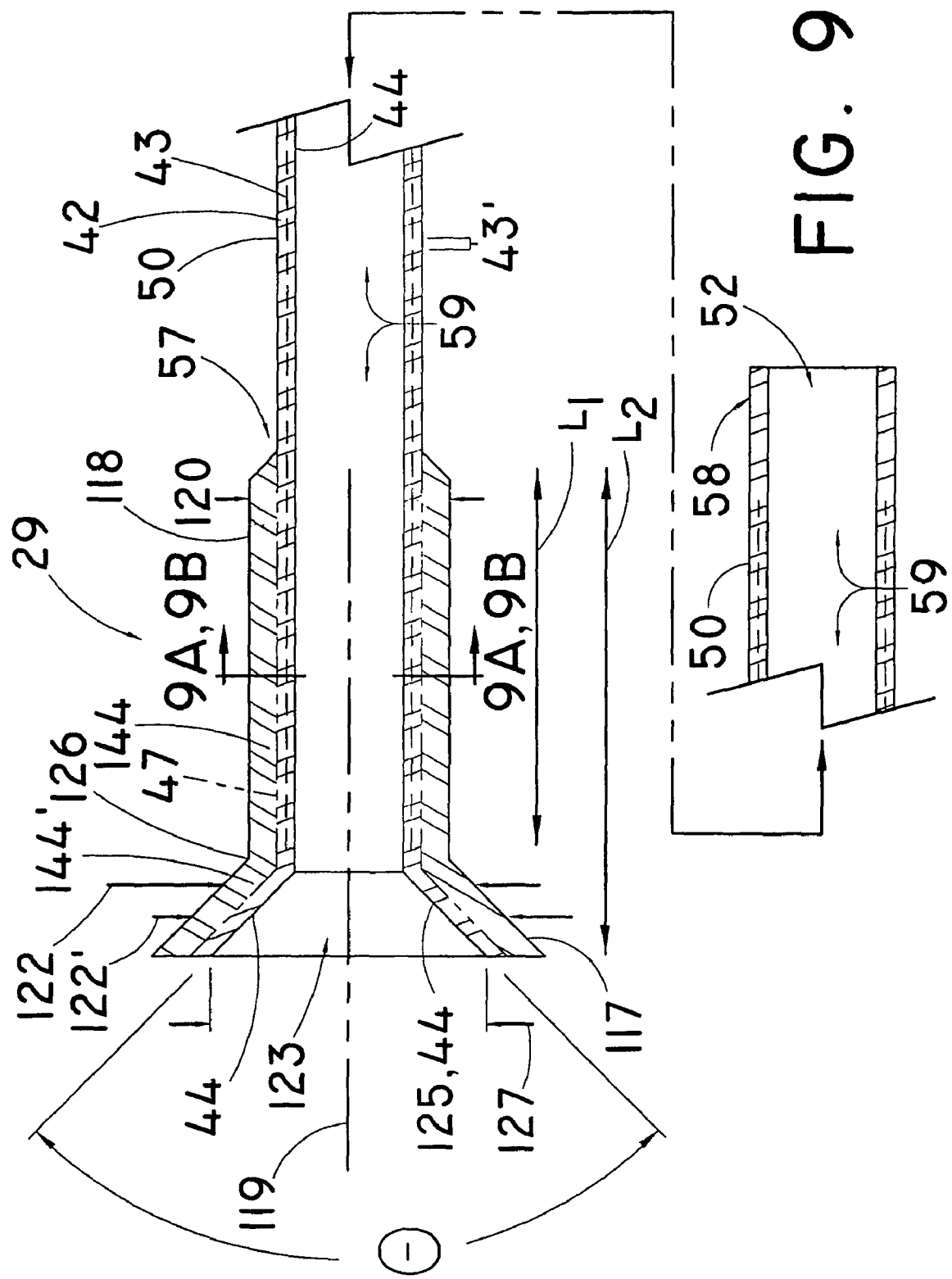
FIG. 9 shows a longitudinally sectioned side view, broken away, of a strain relief member operatively coupled to a proximal end portion of an outer sheath according to one embodiment.
Figure 9C:
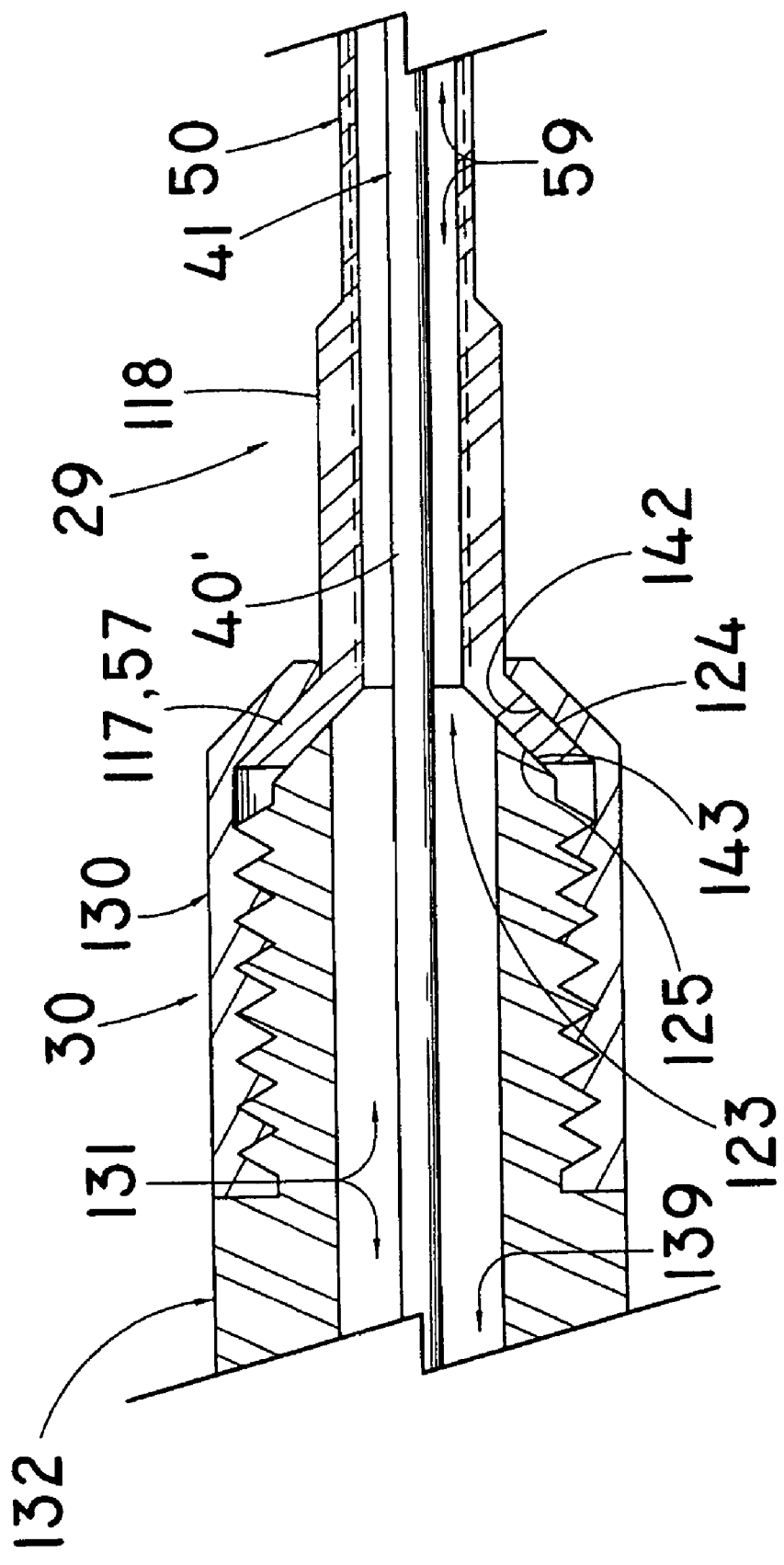
FIG. 9C shows a flared strain relief member having a second end portion operatively coupled between a handle first connector and a handle second connector according to one embodiment.

More particularly, FIGS. 8, 8A, 9, 9A, 9B, and 9C show the portion of the system proximal portion 12 corresponding to FIGS. 1 and 2, and marked illustratively by the broken circle labeled FIG. 9C in FIG. 1. Against that backdrop, FIGS. 8, 8A, 9, 9A, 9B, and 9C are discussed below.

FIG. 8 shows an exploded longitudinally sectioned side view of one embodiment of a portion of the handle comprising a first connector 130 and a second connector 132. In one embodiment, the handle first connector 130 is from a class of fasteners such as nuts, and in one embodiment is a flare nut. The handle first connector 130 further comprises a proximal end 134 and a system distal portion 136. An opening 138 at the proximal end 134 and an opening 140 at the system distal portion 136 define a lumen 133 therebetween. There is an engaging surface 142 at or near the system distal portion 136. A threaded first piece 146 is disposed within the lumen 133 and intermediate the handle first connector distal end opening 140 and proximal end opening 138. The handle second connector 132 further comprises a proximal end 135 and a system distal portion 137. An opening 141 at the system distal portion 137 and an opening 139 (e.g., FIG. 2) at the proximal end 135 define a lumen 131 therebetween. There is an engaging surface 143 at or near the system distal portion 137. A threaded second piece 145 is disposed on the outside surface and intermediate the handle second connector distal end opening 141 and proximal end opening 139.

According to one embodiment shown in FIGS. 8 and 8A, the second connector system distal portion 137 is received within the first connector proximal end opening 138. The first connector 130 and second connector 132 are operatively coupled by a threading engagement between the first connector threaded first piece 146 and the second connector threaded second piece 145. Alternatively, the first connector 130 and second connector 132 are operatively coupled mechanically, chemically, and/or chemical-mechanically. In one embodiment for example, the first connector 130 and second connector 132 are crimped, friction fit, press fit, and/or wedged into engagement. In another embodiment for example, the first connector 130 and second connector 132 are operatively coupled by glue, adhesives, resins, welding (laser, spot, etc.), soldering, brazing, adhesives, chemical bonding materials, or combinations thereof.

FIG. 8A shows the second connector threaded second piece 145 operatively coupled to the first connector threaded first piece 146 such that the second connector proximal end 135 is proximal to the first connector proximal end 134 and the second connector system distal portion 137 is located at or near the first connector system distal portion 136. As shown in FIG. 8A, the second connector engaging surface 143 is spaced proximal to the first connector engaging surface 142 for receiving and compressing the flared strain relief member second end portion therebetween.

FIG. 9 shows one embodiment of a flared strain relief member 29 to be used with a medical device delivery system for deploying an implantable prosthesis (e.g., a self-expanding, balloon expandable, or non-expanding stent; prosthetic valve devices, and other implantable articles) at a selected location inside a patient's body. Like elements from the previous drawings, embodiments, and description from above are labeled the same. The medical device delivery system includes an elongate outer sheath 50 (FIGS. 3, 4, 5, 6, 7, 9). The term elongate is used, not lexicographically but instead, to describe embodiments according to the embodiment that are at least about 50.0 cm and having lengths more fully discussed above.

More particularly, FIG. 9 shows that the outer sheath 50 comprises a proximal end portion 57 having an opening 53 and a distal end portion 58 having an opening 52. The distal end portion opening 52 and proximal end portion opening 53 define a passageway 59 therebetween. In one exemplary embodiment, the outer sheath proximal end portion 57 comprises an inner layer 44, a coil 43 forming a plurality of turns positioned longitudinally around the inner layer 44, and spacings 43' between the turns and discontinuing distal to the proximal end portion opening 53. An outer layer 42 is positioned longitudinally around the coil 43 and melt bonded to the inner layer 44 through the coil spacings 43' (see FIGS. 3 and 8). As FIG. 9 depicts, the outer sheath proximal end portion 57 has an outer layer 42 comprising a first melt bonding material.

Melt-bonding material(s) may, by way of example only and not by way of limitation, include one or combination of nylon, nylon natural tubing, polyether block amide (PEBA), polyetheretherketone (PEEK), thermoplastic, acrylonitrile-butadiene-styrene copolymer (ABS plastic), polypropylene, polyamide, ionomer, polycarbonate, polyphenylene oxide (PPO), polyphenylene sulphide (PPS), acrylic, liquid crystal polymer (LCP), polyolefin, polyethylene acrylate acid, polyvinylidene fluoride (PVDF), polyvinyl, and polyvinyl chloride (PVC) (collectively and individually, "nylon" and/or "PEBA"). Pebax® PEBA is one commercially available melt-bonding material, and is available from the Arkema Group.

The first and second melt-bonding materials may be the same or substantially the same materials. In the alternative, the first and second melt-bonding materials may be different, so long as they have substantially similar melting points at standard atmospheric pressure such that the materials soften (or liquefy) under heat and thereby fuse together in a solid state melt bond 47 joining the first and second melt bonding materials of the outer sheath outer layer 42 and the strain relief member first end portion 118, respectively. If the materials had melting points that were too different, then one material may degrade or burn and the like before the second material begins to melt.

According to FIG. 9, a strain relief member 29 comprises a tubular first end portion 118 and a flared second end portion 117. The first end portion 118 has a first outer diameter 120, while the second end portion 117 has a variable second outer diameter 122, 122' greater than the first outer diameter 120. The first end portion 118 has an inner engaging surface 144 disposed concentrically about the outer sheath proximal end portion outer layer 42 and comprising a second melt bonding material. The strain relief member second end portion 117 is flared in one embodiment to an angle θ, where angle θ is at least 30 degrees. For instance, the strain relief member second end portion 117 has an inner diameter that is flared at least about 30 degrees relative to the longitudinal axis 119. In addition, the strain relief member second end portion 117 comprises an opening 123 in fluid communication with the outer sheath passageway 59 at or near the outer sheath proximal end portion 57.

The second end opening 123 may comprise an inner engaging surface 144' of the strain relief member second end portion 117. Alternatively, the second end opening 123 may comprise the outer layer 42 of the outer sheath proximal end portion 57, whereby the strain relief member second end portion inner engaging surface 144' optionally disposes about and operatively couples by a melt bond 47 to the outer sheath outer layer 42. In yet another embodiment, the second end opening 123 may comprise the inner layer 44 of the outer sheath proximal end portion 57, whereby the strain relief member second end portion inner engaging surface 144' optionally disposes about and operatively couples by a melt bond 47 to the outer sheath inner layer 44.

A flared description of the strain relief member second end portion 117 comprises variable outer diameters 122, 122' (FIG. 9) that are greater than the strain relief member first end portion outer diameter 120 (FIG. 9). Accordingly, the strain relief member 29 is a flared strain relief member. It should also be understood that the second end portion 117 is flared to the extent that it optionally has at least one inner diameter 127 greater than the first end portion outer diameter 120.

In general, the strain relief member 29 has a first end portion 118 that has a length L1 of at least about 10.0 mm as measured along the longitudinal axis 119. In one embodiment, the second end portion 117 has a flared angle θ and the sum of the lengths of the first and second end portions 118, 117, respectively, is a length L2 that is from about 10.0 mm to about 15.0 mm as measured along the longitudinal axis 119. In one embodiment, the first end portion 118 and/or its corresponding inner engaging surface 144 has a length L1, which length L1 is at least about 5.0 mm longer than the length of the second end portion 117. Although the length of the first end portion 118 and/or its corresponding inner engaging surface 144 may vary, optimally it is at least twice as long as the outer diameter of the outer sheath proximal end that it disposes about, so as to have sufficient holding power. In one embodiment, the strain relief member first end portion 118 is at least 0.004 inches in thickness. Likewise, the strain relief member second end portion 117 may be at least 0.004 inches in thickness.

The strain relief member second end portion 117 and first end portion 118 may be integrally formed to comprise a one piece strain relief member 29 comprising any one or combination of melt bonding materials discussed above. In one embodiment by way of example, the strain relief member second end portion 117 comprises an inner engaging surface 144' contiguous with the strain relief member first end portion inner engaging surface 144 and being formed of the second melt bonding material. The strain relief member second end portion inner engaging surface 144' is disposed about the outer layer 42 of the outer sheath proximal end portion 57, wherein a solid state melt bond 47 joins the first and second melt bonding materials of the outer sheath outer layer 42 and the strain relief member first end inner engaging surface 144', respectively. In that embodiment, the strain relief member second end portion opening 123 comprises the outer sheath outer layer 42 and/or coil 43 in fluid communication with the outer sheath passageway 59. In another embodiment, the strain relief member second end portion inner engaging surface 144' is disposed about a portion of the outer sheath inner layer 44 without a coil, and operatively coupled such that the strain relief member second end portion opening 123 comprises the outer sheath inner layer 44 and is in fluid communication with the outer sheath passageway 59. In still another embodiment, the strain relief member second end portion inner engaging surface 144' extends proximally from the outer sheath proximal end portion 57 and is contiguous with the strain relief member first end portion inner engaging surface 144, such that the second end portion opening 123 comprises the strain relief member first end portion inner engaging surface 144 in fluid communication with the outer sheath passageway 59.

As alternatives to a contiguous strain relief member 29, the strain relief member second end portion 117 and first end portion 118 may be separate and are operatively coupled at a joint 126 by a melt bond 47 or any suitable means, such as such as glue, adhesives, resins, welding, soldering, brazing, adhesives, chemical bonding materials, crimp, clamp, pinchers, teeth, friction fit, press fit tight, nesting, wedge, or combinations thereof and the like. When operatively coupled at a joint 126, the second end portion 117 and/or the first end portion 118 may be made of any suitable material (natural, synthetic, thermosetting or thermoforming plastic, rubber, metal, or combination thereof) that is rigid, strong, and resilient. For instance, the second end portion 117 may be a rigid, strong, resilient plastic or metal preformed to a flared angle θ and operatively coupled at a joint 126 to the first end portion 118 that comprises melt bonding material joined by a melt bond 47 to the outer sheath proximal end portion 57. In another alternative, the second end portion 117 comprises melt bonding material joined by a melt bond 47 to the outer sheath proximal end portion 57 such that the strain relief member second end portion opening 123 comprises the outer sheath inner layer 44 and/or coil 43 in fluid communication with the outer sheath passageway 59, whereas the strain relief member first end portion 118 is made of a rigid, strong, resilient plastic or metal and disposes about and operatively couples to the outer sheath proximal end portion 57 outer layer 44 and/or coil 43 by glue, adhesives, resins, welding, soldering, brazing, adhesives, chemical bonding materials, crimping, clamping, pincher, teeth, friction fit, press fit tight, nesting, wedge, or combinations thereof and the like.

FIG. 9A shows a cross section taken along the line 9A-9A in FIG. 9. In FIG. 9A, the first end portion inner engaging surface 144 is disposed concentrically about the outer sheath proximal end outer layer 42 prior to melt bonding. FIG. 9A also includes the outer sheath coil 43, inner layer 44, passageway 59.

FIG. 9B also shows a cross section taken along the line 9A-9A in FIG. 9. In FIG. 9B, the first end portion inner engaging surface 144 has been melt bonded 47 to the outer sheath proximal end portion outer layer 42.

FIG. 9C shows the flared strain relief member second end portion 117 being operatively coupled between the first connector 130 and the second connector 132, and the second connector lumen 131 being in fluid communication with the outer sheath passageway 59. In one embodiment, the flared strain relief member second end portion 117 comprises a first opposing surface 124 and a second opposing surface 125. The first connector engaging surface 142 is disposed against the flared strain relief first opposing surface 124 and the second connector engaging surface 143 is disposed against the flared strain relief second opposing surface 125, whereby the flared strain relief member second end portion 117 becomes operatively coupled between the first and second connector engaging surfaces 142, 143, respectively. In one embodiment, the operatively coupled flared strain relief member second end portion 117 is compressed (e.g., sandwiched) between the first and second connector engaging surfaces 142, 143.

In the embodiment of the strain relief member 29 where the second end portion inner engaging surface 144' (FIG. 9) is disposed about the outer layer 42 (FIG. 9) of the outer sheath proximal end portion 57 to form a solid state melt bond 47 (FIG. 9), the strain relief member second end portion second opposing surface 125 comprises the outer sheath outer layer 42 (FIG. 9), which is disposed against the second connector engaging surface 143. In the alternative embodiment where the second end portion inner engaging surface 144' (FIG. 9) is disposed about and operatively coupled to the inner layer 44 (FIG. 9) of the outer sheath proximal end portion 57 (FIG. 9), the strain relief member second end portion second opposing surface 125 comprises the outer sheath inner layer 44 (FIG. 9), which is disposed against the second connector engaging surface 143. In still another embodiment where the strain relief member second end portion inner engaging surface 144' extends proximally from the outer sheath proximal end portion 57, the strain relief member second end portion inner engaging surface 144' comprises the second opposing surface 125 that is disposed against the second connector engaging surface 143.

An elongate inner compression member 41 comprises a proximal end 40 (FIG. 2) and a middle section 40' (FIG. 9C). The elongate inner compression member proximal end 40 is operatively coupled to an optional stylet 20 (FIGS. 1 and 2) projecting proximally from the handle 30 (FIGS. 1 and 2) and intended to remain outside said patient, the elongate inner compression member 41 and 20 stylet being described above. FIG. 9C shows the inner compression member middle section 40' extending through the handle second connector lumen 131, through the flared strain relief member second end portion opening 123, and within outer sheath passageway 59 such that the outer sheath 50 is axially slideable relative to the inner compression member 41 upon corresponding axial slideable movement of the handle.

The elongate inner compression member 41 further comprises a distal mating end portion 48 (FIGS. 4, 5, 6, 7) that extends at least about 50.0 cm distal from the handle 30. The distal mating end portion 48 is operatively coupled at or near a second end portion 77 of an inner guide channel member 70 that comprises the second end portion 77 and a first end portion 78, an inner guide channel member entry port 72 at the first end portion 78 and an exit port 73 at the second end portion 77 defining a channel 71 therebetween. The inner guide channel member further comprises a stent mounting region 90 (FIGS. 4, 5, 6, 7) intermediate the entry and exit ports 72, 73, respectively. The stent mounting region 90 comprises a platform 91 disposed about the outer guide channel member (FIGS. 4, 5, 6, 7). The stylet 20 and inner compression member 41 are capable of transferring tensile and compressive forces to an inner guide channel member 70 (FIGS. 4, 5, 6, 7) while the handle 30 and outer sheath 50 move axially relative to the inner compression member 41 and the inner guide channel member 70.

In one embodiment, an outer guide channel member 80 is operatively coupled to the outer sheath 50 at or near the outer sheath distal end portion 58 (FIGS. 4, 5, 6, 7). The outer guide channel member has a first end portion 88 and a second end portion 87, an entry port 82 intermediate the first and second end portions 88, 87, respectively, and an exit port 83 at or near the second end portion 87, the entry port 82 and exit port 83 being in fluid communication with a channel 81 therebetween. The outer guide channel member 80 has an inner surface 92 such that the implantable prosthesis is disposed between inner guide channel member platform 91 and the outer member inner surface 92 (e.g., help to maintain the stent until desired deployment). The outer guide channel member second end portion 87 is operatively coupled to the outer sheath distal end portion 58 by a melt bond or any suitable means, such as such as glue, adhesives, resins, welding, soldering, brazing, chemical bonding materials, crimp, clamp, pinchers, teeth, friction fit, press fit tight, nesting, wedge, or combinations thereof and the like. The stylet 20 and inner compression member 41 are capable of transferring tensile and compressive forces to an inner guide channel member 70 (FIGS. 4, 5, 6, 7) while the outer guide channel member 80 is axially slideable relative to the inner guide channel member 70 upon corresponding axial slideable movement of the handle 30.

FIGS. 10, 11, and 12 show alternative perspective embodiments of a flared strain relief member 29 according to FIG. 8. While FIG. 9 showed the strain relief member second end portion 117 to be a conical shape, in another embodiment according to FIG. 10 the strain relief member second end portion 117 may be a flared circular shape relative to a longitudinal axis 119. The strain relief member second end portion 117 may also have a flared rectangular or other polygonal shape relative to a longitudinal axis 119 as in FIG. 11, or may have a slit 121 across the opening 123 to form at least two tails 121', 121" (more slits may be used to form additional tails if desired) that are flared relative to a longitudinal axis 119.

Method

Methods of manufacturing a flared strain relief member for a medical device delivery system for delivering an implantable prosthesis (e.g., a self-expanding, balloon expandable, or non-expanding stent; prosthetic valve devices, and other implantable articles) at a selected location inside a patient's body are also provided.

FIG. 13A shows one method 200 of making a flared strain relief member for a medical device delivery system comprising the step of providing (step 202) an elongate outer sheath 50. The sheath 50 comprises a proximal end portion 57 having an opening 53 and a distal end portion 58 having an opening 52, the openings defining a passageway 59 therebetween. The proximal end portion 57 has an outer engaging surface 42 comprising a first melt bonding material.

FIG. 13B shows a longitudinal sectional view of the outer sheath proximal end portion 57. A mandrel 203 is positioned (step 204) within the sheath proximal end opening 53 and partially within the sheath passageway 59.

FIG. 13C provides (step 206) a strain relief member 29 (shown in a longitudinally sectioned side view) having a first end portion 118 having an outer diameter 120 and an opening 120' and a second end portion 117 having an opening 123 and defining a lumen 128 therebetween and an inner engaging surface 144 comprising second melt-bonding. The strain relief member having a length of at least 10.0 mm along a longitudinal axis 119. The first end portion opening 120' is sized to receive the outer sheath proximal end portion 57 within the strain relief member lumen 128.

FIG. 13D shows disposing (step 208) at least the strain relief member inner engaging surface 144 about the outer sheath proximal end outer engaging surface 42. In one embodiment, the inner engaging surface 144 of the first end portion 118 is disposed about the outer sheath proximal end outer engaging surface 42 while the strain relief member second end portion 117 extends proximally from the outer sheath proximal end portion 57. In another embodiment, the strain relief member first and second end portions 118, 117, respectively, are disposed about the outer sheath proximal end portion 57, as shown in FIG. 13D.

FIG. 13E shows disposing (step 210) a shrink material 211 about at least the strain relief member first end portion 118. In another embodiment, the shrink material 211 may dispose about strain relief member first and second end portions 118, 117, respectively, as shown in FIG. 13E. In one embodiment, the shrink material 211 may be a tube, while in an alternative embodiment the shrink material 211 may be a sheet that is wrapped into a tube or otherwise wrapped about strain relief member first and second end portions 118, 117, respectively. FIG. 13E also shows heating (step 212) the outer sheath proximal end outer engaging surface 42 and the strain relief member inner engaging surface 144 sufficient to melt the first and second melt-bonded materials together.

The outer sheath proximal end outer engaging surface 42 and the strain relief member inner engaging surface 144 melt bonded by any suitable means, such as heat. For instance, a radiofrequency loop heater may be used for the heating step 212 to melt the outer sheath proximal end outer engaging surface 42 and the strain relief member inner engaging surface 144. Such a machine is available from Magnaforce, Incorporated and sold under the name and model Heatstation 1500. Another such machine is available from Cath-Tip, Inc., and is sold under the model and name Cath-Tip II.

Materials have different "melt bonding" temperatures at which the material will soften and become almost tacky without substantial degradation. The strain relief member 29 provided in step 206 may comprise one or a combination of melt-bonding material such as nylon, nylon natural tubing, polyether block amide, polyetheretherketone, thermoplastic, acrylonitrile-butadiene-styrene copolymer, polypropylene, polyamide, ionomer, polycarbonate, polyphenylene oxide, polyphenylene sulphide, acrylic, liquid crystal polymer, polyolefin, polyethylene acrylate acid, polyvinylidene fluoride, polyvinyl, and polyvinyl chloride.

In one embodiment where PEEK tubing is used for the strain relief member 29, because PEEK melts at about 633° F., the inner guide channel member second end portion 77 is heated from about 628° F. to about 638° F. There is a rise dwell and cool down time for the process. The total rise time is approximately 20 seconds and dwell time is approximately 10 seconds. During the dwell time the temperature is approximately 600 F. In one embodiment where nylon or PEBA are used for the strain relief member 29, heating step 212 is at about 400° F. The dwell time heating step 212 is about 10 seconds.

The method of further comprises the step of cooling the first and second melt-bonded materials to solid state to form a melt bond operatively coupling at least the inner engaging surface of strain relief member first end portion and the outer sheath outer engaging surface. The method further comprises the step of removing the shrink material. In another step, the mandrel is removed.

FIG. 13F shows inserting (step 214) a flaring iron 215 within the strain relief member second end portion opening 123. The flaring iron is heated to a temperature at or near the melting point at standard atmosphere for the outer sheath proximal end outer engaging surface 42 and the strain relief member inner engaging surface 144 to flare 216 the second end portion 117 to a variable second end diameter 122, 122' (e.g., FIG. 9) greater than the first end portion first outer diameter 120 (e.g., FIG. 9). The flaring iron is removed and the strain relief member second end portion is cooled to solid state comprising an opening 123 in fluid communication with the outer sheath passageway (e.g., FIG. 9).

Of course, the strain relief member second end portion 117 may be flared to a predetermined outer diameter by placing it in a die that is conical, circular, rectangular, or other desired shape to produce a flared strain relief member having the desired angle θ (FIG. 9). Likewise, the flared strain relief member 29 may be formed by directly molding it onto the outer sheath outer layer 42 by placing the outer sheath proximal end portion 57 into a jig having an inner diameter greater than the outer sheath proximal end portion 57 (the difference being the desired thickness of the strain relief member 29), closing up the jig, and injecting melt bonding material such that the outer sheath proximal end outer engaging surface 42 and the strain relief member inner engaging surface 144 sufficient to melt the first and second melt-bonded materials together.

A method of manufacturing and of providing a medical device as taught herein for delivering a self-expanding stent need not be performed sequentially. By way of example, the mandrel 203 may be provided (step 204) before the outer sheath 50 is provided (step 202). The strain relief member 29 may be provided (step 206) before either the mandrel 203 or outer sheath is provided (steps 204, 202, respectively).

It is intended that the foregoing detailed description of a flared strain relief member for use with medical device delivery systems and medical devices, and methods of forming the flared strain relief member, disposed about a proximal end portion of an elongate sheath be regarded as illustrative rather than limiting, and that it be understood that it is the following claims, including all equivalents, that are intended to define the spirit and scope of this invention. Terms are to be given their reasonable plain and ordinary meaning. Also, the embodiment of any figure and features thereof may be combined with the embodiments depicted in other figures. Other features known in the art and not inconsistent with the structure and function of the present invention may be added to the embodiments.

While particular elements, embodiments, and applications of the present invention have been shown and described, it will be understood, of course, that the invention is not limited thereto since modifications may be made by those skilled in the art, particularly in light of the foregoing teachings. Therefore, it is therefore contemplated by the appended claims to cover such modifications as incorporate those features which come within the spirit and scope of the invention.

What is claimed is:

1. A strain relief member for a medical device delivery system comprising:
   an elongate outer sheath comprising a proximal end portion having a flared outer diameter and a proximal opening and a distal end portion having a distal opening, the proximal and distal openings defining an outer sheath passageway therebetween, the proximal end portion being flared to an angle θ with respect to a longitudinal axis of the outer sheath and having an outer layer comprising a first melt bonding material;
   a strain relief member comprising a tubular first end portion having a first outer diameter and a flared second end portion with a variable second outer diameter greater than the first outer diameter, the flared second end portion of the strain relief member having an inner engaging surface disposed concentrically about the outer layer of only the proximal end portion of the outer sheath and comprising a second melt bonding material, the flared second end portion being flared to the angle θ and comprising an opening in fluid communication with the outer sheath passageway; and
   a melt bond joining the first and second melt bonding materials.

2. The strain relief member of claim 1 wherein the flared second end portion and tubular first end portion are integrally formed to comprise a one piece strain relief member.

3. The strain relief member of claim 1 wherein the flared second end portion comprising the inner engaging surface formed of the second melt bonding material is melt bonded to the outer layer of the proximal end portion of the outer sheath.

4. The strain relief member of claim 1 wherein the flared second end portion and the tubular first end portion are operatively coupled at a joint.

5. The strain relief member of claim 1 wherein the strain relief member has a length of ranging from about 10.0 mm to about 15.0 mm along a longitudinal axis, the inner engaging surface of the tubular first end portion comprising at least about 5.0 mm said length and being disposed concentrically about the outer layer of the proximal end portion of the outer sheath.

6. The strain relief member of claim 1 wherein the angle θ is at least about 30 degrees relative to the longitudinal axis.

7. The strain relief member of claim 6 wherein the flared second end portion comprises a conical shape.

8. The strain relief member of claim 1 wherein the tubular first end portion has a thickness of at least about 0.004 inches.

9. The strain relief member of claim 1 wherein with the first and second melt bonding materials have substantially similar melting points at standard atmospheric pressure.

10. The strain relief member of claim 9 wherein the first and second melt-bonding materials are selected from the group consisting of nylon, nylon natural tubing, polyether block amide, polyetheretherketone, thermoplastic, acrylonitrile-butadiene-styrene copolymer, polypropylene, polyamide, ionomer, polycarbonate, polyphenylene oxide, polyphenylene sulphide, acrylic, liquid crystal polymer, polyolefin, polyethylene acrylate acid, polyvinylidene fluoride, polyvinyl, and polyvinyl chloride.

11. The strain relief member of claim 1, wherein the first melt bonding material and the second melt bonding material are the same material.

12. The strain relief member of claim 1, wherein the first melt bonding material and the second melt bonding material are different materials having substantially similar melting points at standard atmospheric pressure.

13. The strain relief member of claim 1, wherein the melt bond comprises a fused portion of the first and second melt bonding materials formed by softening the first and second melt bonding materials under heat and then cooling to solid state.

14. A medical device delivery system for deploying an implantable prosthesis at a selected location inside a patient's body, the delivery system comprising:
   an elongate outer sheath having a proximal end portion having a flared outer diameter and a distal end portion defining an outer sheath passageway therebetween, the proximal end portion comprising a first melt bonding material and being flared to an angle θ with respect to a longitudinal axis of the outer sheath;
   a flared strain relief member having a first end portion with a first outer diameter and a second end portion with a larger second outer diameter, the first end portion comprising a second melt bonding material and being disposed about and operatively coupled to only the proximal end portion of the outer sheath via a melt bond joining the first and second melt bonding materials, and the second end portion having an inner engaging surface disposed concentrically about the proximal end portion of the outer sheath and being flared to the angle θ the second end portion further comprising an opening in fluid communication with the outer sheath passageway;
   a handle comprising a first connector having a first connector lumen and a second connector having a second connector lumen, the second end portion of the flared strain relief member being operatively coupled between the first connector and the second connector, and the second connector lumen being in fluid communication with the outer sheath passageway.

15. The delivery system of claim 14 wherein the first end portion of the flared strain relief member comprises an inner engaging surface and is disposed concentrically about an outer layer of the proximal end portion of the outer sheath.

16. The delivery system of claim 14 wherein the first connector further comprises a proximal end and a distal end, openings at the proximal and distal ends defining a lumen, an engaging surface at or near the distal end, and a threaded first piece, and the second connector further comprises a proximal end and a distal end, openings at the proximal and distal ends defining a lumen, an engaging surface at or near the distal end, and a threaded second piece, and further wherein the distal end of the second connector is received within the opening at the proximal end of the first connector, the threaded second piece being operatively coupled to the threaded first piece.

17. The delivery system of claim 16 wherein the engaging surface of the first connector is disposed against a first opposing surface of the second end portion of the flared strain relief member and the engaging surface of the second connector is disposed against a second opposing surface of the second end portion of the flared strain relief member.

18. The delivery system of claim 14 further comprising an elongate inner compression member having a proximal end, a middle section, and a distal end portion, the middle section extending through the second connector lumen and the outer sheath passageway, wherein the outer sheath is axially slideable relative to the inner compression member upon corresponding axial slideable movement of the handle, and further wherein the elongate inner compression member extends at least about 50.0 cm distally from the handle and comprises a distal mating end portion operatively coupled to an inner guide channel member having a first end portion and a second end portion and defining a channel therebetween and comprising a stent mounting region.

19. The delivery system of claim 18 wherein the proximal end of the elongate inner compression member is operatively coupled to a stylet projecting proximally from the handle and intended to remain outside said patient, the stylet and inner compression member being capable of transferring tensile and compressive forces to the inner guide channel member while the handle and outer sheath move axially relative to the inner compression member.

20. The delivery system of claim 18 further comprising an outer guide channel member having a first end portion and a second end portion, the second end portion being operatively coupled to the distal end portion of the outer sheath, the outer guide channel member having an entry port at or near the first end and an exit port at or near the second end portion, the ports being in fluid communication with the channel therebetween, and the outer guide channel member being operatively coupled to the distal end portion of the outer sheath and slideable relative to the inner guide channel member with proximal movement of the handle.

21. The strain relief member of claim 14, wherein the second end portion of the flared strain relief member is sandwiched between engaging surfaces of the first connector and the second connector.

\* \* \* \* \*